United States Patent
Perucho et al.

(12)

(10) Patent No.: US 6,566,053 B1
(45) Date of Patent: May 20, 2003

(54) IDENTIFICATION OF NEOPLASMS BY DETECTION OF GENETIC INSERTIONS AND DELETIONS

(75) Inventors: Manuel Perucho, San Diego, CA (US); Miguel Angel Peinado, Barcelona (ES); Yurij Ionov; Sergei Malkhosyan, both of San Diego, CA (US); Michael McClelland, Encinitas, CA (US); John Welsh, Leucadia, CA (US)

(73) Assignee: Stratagene, La Jolla, CA (US)

( * ) Notice: Subject to any disclaimer, the term of this patent is extended or adjusted under 35 U.S.C. 154(b) by 1096 days.

(21) Appl. No.: 08/579,445

(22) Filed: Dec. 27, 1995

Related U.S. Application Data

(63) Continuation of application No. 08/152,484, filed on Nov. 12, 1993, now abandoned, which is a continuation-in-part of application No. 07/975,737, filed on Nov. 13, 1992, now abandoned.

(51) Int. Cl.$^7$ .............................. C12Q 1/68; C12P 19/34
(52) U.S. Cl. .......................................... 435/6; 435/91.2
(58) Field of Search .............................. 435/91.1, 91.2, 435/6; 536/24.1; 436/813

(56) References Cited

U.S. PATENT DOCUMENTS

| | | | |
|---|---|---|---|
| 4,666,828 A | 5/1987 | Gusella | |
| 5,075,214 A | 12/1991 | Connor et al. | |
| 5,098,823 A | 3/1992 | Bodmer et al. | |
| 5,380,645 A | 1/1995 | Voglestein | |
| 5,578,450 A | * 11/1996 | Thibodeau et al. | ............ 435/6 |

FOREIGN PATENT DOCUMENTS

| | | |
|---|---|---|
| EP | 0390324 | 10/1990 |
| FR | 2680520 | 8/1991 |
| WO | 9002203 | 3/1990 |
| WO | 9216662 | 10/1992 |
| WO | 9320233 | 10/1992 |
| WO | 9304200 | 3/1993 |
| WO | 9320238 | 10/1993 |
| WO | WO 94/11531 | 5/1994 |

OTHER PUBLICATIONS

Almoguera, C., et al. (1988) Most human carcinomas of the exocrine pancreas contain mutant c–K–ras genes. *Cell* 53:549–554.
Baker, S.J., et al. (1989) Chromosome 17 deletions and p53 gene mutations in colorectal carcinomas. *Science* 244:217–221.
Barany, F. (1991) Genetic disease detection and DNA amplification using cloned thermostable ligase. *Proc. Ntl. Acad. Sci. USA* 88:189–193.
Bishop, J.M. (1991) Molecular themes in oncogenesis. *Cell* 64, 235–248.
Bos, J.L., et al. (1987) Prevalence of ras gene mutations in human colorectal cancer. *Nature* 327:293–297.
Bos, J. (1989) Detection of ras oncogenes using PCR. *PCR Technology*, ed. Erlich, H.A. (Stockton, New York), pp. 225–233.
de Jong, D., et al. (1988) Somatic changes in B–lymphoproliferative disorders (B–LPD) detected by DNA–fingerprinting. *Br. J. Cancer* 58, 773–775.
Fearon, E.R., et al. (1990) Identification of a chromosome 18q gene that is altered in colorectal cancers. *Science* 247:49–56.
Fearon, E.R., et al. (1990) A genetic model for colorectal tumorigenesis. *Cell* 61:759–767.
Fey, M.F., et al. (1988) Assessment of clonality in gastrointestinal cancer by DNA fingerprinting. *J. Clin. Invest.* 82:1532–1537.
Forrester, K., et al. (1987) Detection of high incidence of K–ras oncogenes during human colon tumorigenesis. *Nature* 327:298–303.
Foulds, L. (1954) The experimental study of tumor progression: A review. *Cancer Research* 14:327–337.
Groden, J. et al. (1991) Identification and characterization of the familial adenomatous polyposis coli gene. *Cell* 66:589–600.
Harris, C.C. (1991) Chemical and physical carcinogenesis: advances and perspectives for the 1990s. *Cancer Research* 51:5023–5044.
Higuchi, R. (1989), Chapter 4, Principles and applications for DNA amplification, ed. Erlich, H.A. (Stockton, N.Y.), pp. 31–36.
Kahn, S.M., et al. (1987) The c–K–ras gene and human cancer. *Anticancer Res.* 7:639–652.
Kinzler, K.W., et al. (1991) Identification of FAP locus genes from chromosome 5q21. *Science* 253:661–665.
Knudson, A.G. (1971) Mutation and cancer: statistical study of retinoblastoma. *Proc. Natl. Acad. Sci. USA* 68:820–823.
Knudson, A.G. (1985) Hereditary cancer, oncogenes and antioncogenes. *Cancer Res.* 45:1437–1443.
Lindahl, T., et al. (1991) Molecular deficiencies in human cancer–prone syndromes associated with hypersensitivity to DNA–damaging agents. *Origins of Human Cancer: A Comprehensive Review*. Cold Spring Harbor Laboratory Press. Brugge, J., Curran, T., Harlow, E., and McCormick, F., eds. pp. 163–170.
Loeb, L.A., et al. (1974) Errors in DNA replication as a basis for malignant changes. *Cancer Research* 34:2311–2321.
Loeb, L.A. (1991) Mutator phenotype may be required for multistage carcinogenesis. *Cancer Res.* 51:3075–3079.

(List continued on next page.)

Primary Examiner—Kenneth R. Horlick
(74) *Attorney, Agent, or Firm*—Finnegan, Henderson, Farabow, Garrett & Dunner, LLP

(57) ABSTRACT

The detection of insertions and/or deletions in reiterated nucleotide sequences in tissues provides an identification of neoplastic changes that are associated with malignancy. The mutations are preferably detected by PCR based amplification of target sequences using selected primers, followed by standard analytic procedures. The detection of these mutations is useful as a diagnostic tool for cancer development and has direct application for cancer prognosis.

39 Claims, 7 Drawing Sheets

OTHER PUBLICATIONS

Nakano, H., et al. (1984) Isolation of transforming sequences of two human lung carcinomas: Structural and functional analysis of the activated c K–ras oncogenes. *Proc. Natl. Acad. Sci. USA* 81:71–75.

Nowell, P. (1976) The clonal evolution of tumor cell populations. *Science* 194:23–28.

Peinado, M.A., et al. (1992) Isolation and characterization of allelic losses and gains in colorectal tumors by arbitrarily primed polymerase chain reaction. *Proc. Natl. Acad. Sci. USA* 89: 10065–10069.

Saiki, R. K., et al. (1985) Enzymatic amplification of β–globin genomic sequences and restriction site analysis for diagnosis of sickle cell anemia. *Science* 230:1350–1354.

Schimke, R.T., et al. (1986) Overreplication and recombination of DNA in higher eukaryotes: potential consequences and biological implications. *Proc. Natl. Acad. Sci USA* 83:2157–2161.

Sinnett, D., et al. (1990) Alumorphs—human DNA polymorphisms detected by polymerase chain reaction using alu–specific primers. *Genomics* 7, 331–334.

Smit, V.T.H.B.M., et al. (1988) Analysis of tumor heterogeneity in a patient with synchronously occurring female genital tract malignancies by DNA flow cytometry, DNA fingerprinting, and immunohistochemistry, *Cancer* 62: 1146–1152.

Thein, S.L., et al. (1987) Detection of somatic changes in human cancer DNA by DNA fingerprint analysis. *Br. J. Cancer* 55:353–356.

Vogelstein, B., et al. (1988) Genetic alterations during colorectal–tumor development. *New England Journal of Medicine* 319:525–532.

Vogelstein, B., et al. (1989) Allelotype of colorectal carcinomas. *Science* 244:207–211.

Weber, J.L., et al. (1989) Abundant class of human DNA polymorphisms which can be typed using the polymerase chain reaction. *Am.J. Hum. Genet.* 44:388–396.

Weinberg, R.A. (1991) Tumor suppressor genes. *Science* 254:1138–1146.

Weinstein, I.B. (1991) Mitogenesis is only one factor in carcinogenesis. *Science* 251:387–388.

Welsh, J., et al. (1990) Fingerprinting genomes using PCR with arbitrary primers. *Nucleic Acids Res* 18:7213–7218.

Welsh, J., et al. (1991) Polymorphism generated by arbitrarily primed PCR in the mouse: application to strain identification and genetic mapping. *Nucleic Acids Res.* 19:303–306.

Williams, J.G.K. et al (1990), DNA polymorphism amplified by arbitrary primers are useful as genetic markers. *Nucleic Acids* Res. 18: 6531–6535.

Jeffreys, et al., (1985) Individual–specific fingerprints of human DNA, *Nature* 316: 76–79.

Mullis, et al., (1986) Specific enzymatic amplification DNA . . . , *Cold Spring Harbor Symp.* LI: 263–273.

Aaltonen, et al., (1993) Clues to the Pathogenesis of Familial Colorectal Cancer, *Science* 260: 812–816.

Beckmann, et al., (1991) Survey of Human and Rat Microsatellites, *Genomics* 12: 627–631.

Hearne, et al., (1991), Microsatellites for linkage analysis of genetic traits, *Trends Genet.* 8: 288–294.

Hudson, et al., (1992), Isolation and Chromosomal Assignment of 100 Highly Informative human Simple Sequence Repeat Polymorphisms, *Genomics* 13: 622–629.

Gehring et al., (1993) A tetrameric DNA structure with protonated cytosine.cytosine base pairs, *Nature* 363: 567–560.

Peltomaki, et al., (1993) Genetic Mapping of a Locus Predisposing to Human Colorectal Cancer, *Science* 260: 810–812.

Thibodeau, et al., (1993) Microsatellite Instability in Cancer of the Proximal Colon, *Science* 260: 816–819.

Weber, (1990) Informativeness of Human $(dG–dA)_n \cdot (dG–dT)_n$ Polymorphisms, *Genomics* 7: 524–530.

Weber, et al., (1993) Mutation of human short tandem repeats, *Human Molecular Genetics* 2: 1123–1128.

Bej, et al., (1991) Amplification of nucleic acids by polymerase, *Crit. Rev. Biochem. Mol. Biol.* 26 (3–4): 301–334.

Aaltonen, L., et al., Replication errors in Benign and Malignant Tumors from Hereditary Nonpolyposis Colorectal Cancer Patients. *Cancer Research* 54: 1645–48 (1994).

Bernues, J. et al., SV40 recombinants carrying a $d(CT–GA)_{22}$ sequence show increased genomic instability. *Gene* 108: 269–74 (1991).

Boman, B. et al., Letter to the Editor: Reassignment of a Cancer Family Syndrome Gene to Chromosome 18. *Cancer Genet Cyogenet* 34:153–4 (1988).

Brook, J. et al., Molecular Basis of Myotonic Dystrophy: Extension of a Trinucleotide (CTG) Repeat at the 3' End of a Transcript Encoding a Protein Kinase Family Member. *Cell* 68:799–808 (1992).

Buffill, J., Colorectal Cancer: Evidence for Distinct Genetic Categories Based on Proximal and Distal Tumor Location. *Ann Int Med.* 113:779–88 (1990).

Burks, R., et al., Microsatellite Instability in endometrial carcinoma. *Oncogene* 9:1163–66 (1994).

Caskey, C.T., et al., Triplet Repeat Mutations in Human Disease. *Science* 256:784–9 (1992).

Dams E., et al., (1995) Instability of Microsatellites in Human Gliomas. *Cancer Research* 55: 1457–49 (1992).

DeLattre, O. et al., Multiple Genetic Alterations in Distal and Proximal Colorectal Cancer. *Lancet* 2:353–56 (1989).

Dracapoli et al., Mapping the Human Analase Gene Cluster on the Proximal Short Arm of Chromosome 1 Using a Highly Informative (CA)n Repeat. *Genomics* 7:97–102 (1990).

Fishel R. et al., The Human Mutator Gene Homolog MSH2 and its Association with Hereditary Nonpolyposis Cancer. *Cell* 75:1027–38 (1993).

Fu, Y. et al., Variation of the CGG Repeat at the Fragile X Site Results in Genetic Instability: Resolution of the Sherman Paradox. *Cell* 67:1047–58 (1991).

Geitvik, G. et al., The Kidd (JK) blood group locus assigned to chromosome 18 by close linkage to a DNA–RFLP. *Human Genet* 77: 205–09 (1987).

Ghahremani, G. et al., Colorectal Carcinomas: Diagnostic Implications of their Changing Frequency and Anatomic Distribution. *World J Surg.* 13:321–25 (1989).

Gonzalez–Zulueta, M. et al., Microsatellite Instability in Bladder Cancer. *Cancer Res.* 53:5620–23 (1993).

Han, H–J, et al., Genetic Instability in Pancreatic Cancer and Poorly Differentiated Type of Gastric Cancer. *Cancer Research* 53:5087–89 (1993).

Hirst, M. et al., Genotype Prediction in the Fragile X Syndrome. *J. Med. Genet.* 28:824–29 (1991).

Jeffreys, A. et al., Individual–Specific Fingerprints of Human DNA. *Nature* 316:76–79 (1985).

Jeffreys, A. et al., Minisatellite Repeat Coding as a Digital Approach to DNA typing. *Nature* 354:204–9 (1991).

Johan, G. et al., The Relationship of DNA Aneuploidy to Molecular Genetic Alterations in Colorectal Carcinoma. *Gastroenterology* 102:1612–19 (1992).

Kern, S. et al., Allelic Loss in Colorectal Carcinoma. *J. Am. Med. Assoc.* 261:3099–3103 (1989).

Kohnoe et al., A systematic survey of repetitive sequences abundantly expressed in rat tumors. *Biochemica et Physica Acta* 909:107–14 (1987).

Kremer et al., Mapping of DNA Instability at the Fragile X to a Trinucleotide Repeat Sequence p(CCG)n. *Science* 252:1711–14 (1991).

La Spada, A. et al., Androgen Receptor Gen Mutations in X–linked Spinal and Bulbar Muscular Atrophy. *Nature* 352:77–79 (1991).

Lagoda et al., Increased Detectability of Somatic Changes in DNA from Human Tumours After Probing with "synthetic" and Genome–Derived Hypervariable Mutilocus Probes. *Hum Genet.* 84:35–40 (1989).

Lynch et al., Hereditary Nonpolyposis Colorecta Cancer (Lynch Syndromes I and II). *Cancer* 56: 939–51 (1985).

Mahadaven, M., et al., Myotonic Dystrophy Mutation: An Unstable CTG Repeat in the 3' Untranslated Region of the Gene. *Science* 255: 1253–55 (1992).

Mandel, J., Questions of Expansion. *Nature Genetics* 4:8–9 (1993).

Mao, L., et al., Molecular Detection of Primary Bladder Cancer by Microsatellite Analysis. *Science* 271:659–662 (1996).

Matsumura, Y. and Tarin, D., DNA Fingerprinting Survey of Various Human Tumors and their Metastases. *Cancer Res.* 52:2174–79 (1992).

Mironov, N., et al. Alterations of $(CA)_n$ DNA Repeats and Tumor Suppressor Genes in Human Gastric Cancer. *Cancer Res.* 54:41–44 (1994).

Miyoshi et al., Somatic Mutations of the APC Gene in colorectal tumors: Mutation cluster region in the APC gene. *Hum Mol Genet.* 1(4):229–33 (1992).

Moen, et al., Scc–1, a novel colon cancer susceptibility gene in the mouse: linkage to CD44 (Ly–24, PgP–1) on chromosome 2. *Oncogene* 7:563–66 (1992).

Mullis et al., Specific Enzymatic Amplificaiton of DNA. *Cold Spring Harbor Symposia on Quantitative Biology.* vol. LI: 263–273 (1986).

Murray et al., Three Different Human Tumor Cell Lines Contain Different Oncogenes. *Cell* 25:355–61 (1981).

Nawroz, H., et al., Microsatellite alterations in serum DNA as head and neck patients. *Nature Medicine* 2(9):1035–1038 (1996).

Nickoloff, Transcription Enhances Intrachromosomal Homologous Recombination in Mammalian Cells. *Mol and Cell Biol.* 12:5311–18 (1922).

Nurnberg et al., DNA fingerprinting with the Oligonucleotide Probe (CAC)5/(GTG)5: Somatic Stability and Germline mutations. *Hum Genet.* 84:75–78 (1989).

Orlow, Il, et al. Chromosome 9 Allelic Losses and Mirosatellite Alterations in Human Bladder Tumors. *Cancer Res.* 54, 2848–51 (1994).

Parsons, R. et al., Hypermutability and Mismatch Repair Deficiency in RER+ Tumor Cells. *Cell* 75: 1227–36 (1993).

Peltomaki, P. et al., Evidence supporting Exclusion of the DCC Gene and a portion of the chromosome 18q as the Locus for Susceptibility to Hereditary Nonpolyposis Colorectal Carcinoma in Five Kindreds. *Cancer Research* 51:4135–40 (1991).

Peltomaki, P. et al., Evidence that the MCC–APC Gene Region in 5q21 is not the Site for susceptibility to Hereditary Nonpolyposis Colorectal Carcinoma. *Cancer Research* 52:4530–33 (1992).

Perucho, M. et al, Human–Tumor–Derived Cell lines Contain Common and Different Transforming Genes. *Cell* 27:467–76 (1981).

Rinsinger, J. et al., Genetic Instability of microsatellites in Endometrial Carcinoma. *Cancer Research.* 53: 5100–03 (1993).

Rogers, B. et al., Analysis of DNA in Fresh and Fixed Tissue by the Polymerase Chain Reaction. *Am. J. Path.* 136:541–48 (1990).

Strand, M. et al. Destabilization of tracts of simple repetitive DNA in yeast by mutations affecting DNA mismatch repair. *Nature* 365:274–75 (1993).

Tautz, D., Hypervariability of Simple Sequences as a General Source for Polymorphic DNA Markers. *Nucleic Acids Res.* 17:6463–71 (1989).

Yee, C., et al. Microsatellite Instability and Loss of Heterozygosity in Breast Cancer. *Cancer Res.* 54:1641–44 (1994).

Weiss, R., Gene for Colon Cancer Identified. *The Washington Post* Dec. 3, 1993: A1.

Weissenbach, J. et al. A second–generation linage map of the human genome. *Nature* 359: 794–801 (1992).

* cited by examiner

AP1

5'
ggagtcgactgtgctataactttttgtgccgacatgtagcatgcttttt
   K3US arbitrary primer tcattaattaagtctatagtcttatctacatttctaaatctaaaaaagag ctctaaatatcacaaaatattttcttgaaaaactcttttggtaaaaaacc tggccttggCTGGGTGcaGTGGCG ACgCCTGTAATCCCAGCACTTTGAGA
         CTGGGcGtgGTGGCTcACaCCTGTAATCCCAGCACTTTGgGA
           ALU consensus sequence..............

GcCtGAGGTGGGcGGATCACCTGAtGTCgGGAGTTCgAGACCAGCCTGAC
GgCcGAGGTGGGtGGATCACCTGAgGTCaGGAGTTCaAGACCAGCCTGgC

CAACATGGaGAAACTCCGTCTCtattaaaacacaaaaTTAGCCaGGtGTG
CAACATGGtGAAACcCCGTCTC                TTAGCCgGGcGTG GTGGCaCatGCCTGTAATCCCAGCTACTtGGGAGGCTGAaGC GGAGAATt
GTGGCgCgcGCCTGTAATCCCAGCTACTcGGGAGGCTGAgGCaGGAGAATc GCTTGAgCCtgGaAGGcaGAGGTTGCgGTGAGCtGAtATtGCaCCAtTGC
GCTTGAaCCcaGgAGGtgGAGGTTGCaGTGAGCcGAgATcGCgCCAcTGC ACTCCAGCCTGGGCAAtAaGAGCGAaACTCCATCTCaaaaaaaaaaaagg
ACTCCAGCCTGGGCAAcA GAGCGAgACTCCATCTC aaaacaacaacCTGGcCtTGGccagTtgcAgtgGctcataTAATCCCAGC
           CTGGgCgTGGtggcTcacAcctG        TAATCCCAGC ACTTTGGGAGGCCcAGaTGGGTGGATCACCTGAGGTCAGGAGTTCgAGAC
ACTTTGGGAGGCCgAGgTGGGTGGATCACCTGAGGTCAGGAGTTCaAGAC CAGCCTGGaCAACATGGTGAAACCCTGTCTCtactaaatactaaagTTAG
CAGCCTGGcCAACATGGTGAAACCCcGTCTC                TTAG CCcGGCATaGTGGCagGtGCCTGTAATCCCAGCTACTtGGGAGGCTGAGG
CCgGGCgTgGTGGCgcGcGCCTGTAATCCCAGCTACTcGGGAGGCTGAGG CAGGAGAATCaCTTGAACCtgGGAGGTGGAGGTTGCAGTGAGCCGAGATC
CAGGAGAATCgCTTGAACCcaGGAGGTGGAGGTTGCAGTGAGCCGAGATC aCGaCgCTGCACTCCAGCCTaGGtgA CAGAGCagGACTCtgTCTCaaaaa
gCGcCaCTGCACTCCAGCCT GGgcAaCAGAGCgaGACTCcaTCTC aaaaaaaaagttatagcacagtcgactcc.
   K3US arbitrary primer                            3'

<u>KpNX AP-PCR primer caac</u> tatttctaattgtatacagctaaatat     27

<u>APΔ2U PCR PRIMER</u>
atgtgtatatctgggtctgaatatgtcttggatatttctcgttaatttat     77 ttcatcttgaaatacaaaagtacaaaagaaatataaaatagccactcatc     127

```
GGCCtGatGTGGTGGCTCACgC TGTAATCCCAGCACTTTGGGAGGCCGA    176
GGCtGGcGTGGTGGCTCACaCcTGTAATCCCAGCACTTTGGGAGGCCGA    ALU
        10        20        30        40        50
```

```
GGTGGGcaGATCAtC  AGGTCAaGAaaTCgAGACCAtCCTGGCCAACAT    224
GGTGGGtgGATCAcCtgAGGTCAgGAgtTCaAGACCAgCCTGGCCAACAT    ALU
        60        70        80        90       100
```

<u>         (Alu)         </u>
```
GGTGAAAtCCtGTCTCTACTAAAAATACAAAAcTTAGCCaGGCaTGGTGG    274
GGTGAAAcCCcGTCTCTACTAAAAATACAAAAaTTAGCCgGGCgTGGTGG    ALU
       110       120       130       140       150
```

```
tGCGtGCCTGTAgTCCCAaCTACTCaGGAGGCTGAGGCAGaAGAATtGCT    324
cGCGcGCCTGTAaTCCCAgCTACTCgGGAGGCTGAGGCAGgAGAATcGCT    ALU
       160       170       180       190       200
```

```
TGAACCtGGGAGtcaGAGGTTGCAGTGAGCCaAGATCaCGCCAttGCACT    374
TGAACCcGGGAGgtgGAGGTTGCAGTGAGCCgAGATCgCGCCAcTGCACT    ALU
       210       220       230       240       250
```

```
CCAGCCTGG tGACAGAGCcAGACTCCGTCTCAAAAAAAAAAAAgaaaaga  423
CCAGCCTGGgcGACAGAGCgAGACTCCGTCTCA(n)                 ALU
       260       270       280       290       300
``` aaaagaaaaaaggcccccc<u>ttttttttttttttt</u>aagatttaggtgattt     473 ta<u>ttttgattttaatttcaatatgatcat</u>cagtgagattta   <u>gttg KpNX</u>
              <u>APΔ2D PCR PRIMER</u>

(K3US ARBITRARY PRIMER) 5' GGAGTCGACTGGTGCTATAACTTTTTT
                                       -27

1                                                                50
 CCAAATCAGTATAAGAAAGGAATGATATCAAAAAAAAAAAAAAAAAAAAGGG
    APΔ3D PCR PRIMER

51
 AGTGGGGAAAGAAGGTGAGGTTGGAAAGGAGAATTGTATCTAAACTCATA

101
 ATTTCTCCGTTTAAGTTACTCAGAATTGCCCGTTGCGTTGTTAAAGTGCA

151
 GATTGCTGGGCCTCACTGTCTGATTCTGGGGATATGGAGTGGGCTCTTCT
APΔ3U PCR PRIMER
201
 AACATTTCTGAGCTGCCACTGCTGCTGGTTTGAAAACCACACTTTGAGAA

202
 CCACCACTGTAGGTAGAGTGGAGACCTCAGAGAAGCTCCAGTGCTGTGCC

251
 AAAGAGTTTGAGCTTCACTCAAGAGCAGCAGGGAGACATTCAGAGCTTGG 301                                                 338
 TGAAGAGGACGGTGATAAGCTTCTATGTACATATTAGG

339
 AGTCAGAGCCAACCTAGGACGTCAC 3' (6U ARBITRARY PRIMER)

FIG. 5

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: 3U (xi) SEQUENCE DESCRIPTION: SEQ ID NO:1:

AAGGGATCCC CCTTGCCGTC C                              21

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
             (B) CLONE: K3US (xi) SEQUENCE DESCRIPTION: SEQ ID NO:2:

GGAGTCGACT GGTGCTATAA CTTTTTT                                              27

(2) INFORMATION FOR SEQ ID NO:3:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vii) IMMEDIATE SOURCE:
             (B) CLONE: 6U (xi) SEQUENCE DESCRIPTION: SEQ ID NO:3:

GTGAGCTCCT AGGTTGGCTC TGACT                                                25

(2) INFORMATION FOR SEQ ID NO:4:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vii) IMMEDIATE SOURCE:
             (B) CLONE: 8D (xi) SEQUENCE DESCRIPTION: SEQ ID NO:4:

CTGAAGGGTG AAATATTCCT CC                                                   22

(2) INFORMATION FOR SEQ ID NO:5:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vii) IMMEDIATE SOURCE:
             (B) CLONE: 10DN (xi) SEQUENCE DESCRIPTION: SEQ ID NO:5:

ATGGCGGGAG GTGACTGAC                                                       19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: KpnX (xi) SEQUENCE DESCRIPTION: SEQ ID NO:6:

CTTGCGGGAG GTGACTGAC                                              19

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: MCG1

(xi) SEQUENCE DESCRIPTION: SEQ ID NO:7:

AACCCTCACC CTAACCCCAA                                             20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: LH1

(xi) SEQUENCE DESCRIPTION: SEQ ID NO:8:

GGATGGAAAA GTTGTATCAT                                             20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
              (B) CLONE: LH2

(xi) SEQUENCE DESCRIPTION: SEQ ID NO:9:

AGACCAATTT CTCTTATGAA                                                    20

(2) INFORMATION FOR SEQ ID NO:10:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (vii) IMMEDIATE SOURCE:
              (B) CLONE: ALU (xi) SEQUENCE DESCRIPTION: SEQ ID NO:10:

GGTGAAATCC TGTCTCTACT AAAAA                                              25

(2) INFORMATION FOR SEQ ID NO:11:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

TATCTGGGTC TGAATATGTC TTGGA                                              25

(2) INFORMATION FOR SEQ ID NO:12:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

TGATCATATT GAAATTAAAA TCAAA                                              25

(2) INFORMATION FOR SEQ ID NO:13:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

GAGGCCCAGC AATCTGCACT                                                           20

(2) INFORMATION FOR SEQ ID NO:14:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AAATCAGTAT AAGAAAGGAA                                                           20

(2) INFORMATION FOR SEQ ID NO:15:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

TAAATGAGTT CTGCAAAACA GG                                                        22

(2) INFORMATION FOR SEQ ID NO:16:

(i) SEQUENCE CHARACTERISTICS:
                (A) LENGTH: 22 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

ATCTTCATGC AATGAAAAAT AC                                                        22

(2) INFORMATION FOR SEQ ID NO:17:

(i) SEQUENCE CHARACTERISTICS:
                (A) LENGTH: 55 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

CGCTATCTAC CGCCATAATA AAAAAAAAAA AAAAAAATTA TCGCCGGATA AGACT      55

(2) INFORMATION FOR SEQ ID NO:18:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

CGCTATCTAC CGCCATAATA AAAAAAAAAA AAAATTATCG CCGGATAAGA CT      52

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

TTTTTTTTTT ATTATGGCGG TAGAT      25

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

GTTATCCGGC GATAATTTTT      20

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

ACCGCCATAA TAAAAAA      17

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:22:

```
AAAAAAAAAT TATCGCCGGA T                                              21
```

(2) INFORMATION FOR SEQ ID NO:23:

(i) SEQUENCE CHARACTERISTICS:
        (A) LENGTH: 779 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: APdel1, upper (xi) SEQUENCE DESCRIPTION: SEQ ID NO:23:

```
GGAGTCGACT GTGCTATAAC TTTTTTGTGC CGACATGTAG CATGCTTTTT TCATTAATTA     60
AGTCTATAGT CTTATCTACA TTTCTAAATC TAAAAAAGAG CTCTAAATAT CACAAAATAT    120
TTTCTTGAAA AACTCTTTTG GTAAAAAACC TGGCCTTGGC TGGGTGCAGT GGCGACGCCT    180
GTAATCCCAG CACTTTGAGA GCCTGAGGTG GCGGATACAC CTGATGTCGG GAGTTCGAGA    240
CCAGCCTGAC CAACATGGAG AAACTCCGTC TCTATTAAAA CACAAAATTA GCCAGGTGTG    300
GTGGCACATG CCTGTAATCC CAGCTACTTG GGAGGCTGAA GCGGAGAATT GCTTGAGCCT    360
GGAAGGCAGA GGTTGCGGTG AGCTGATATT GCACCATTGC ACTCCAGCCT GGGCAATAAG    420
AGCGAAACTC CATCTCAAAA AAAAAAAGG AAAACAACAA CCTGGCCTTG GCCAGTTGCA    480
GTGGCTCATA TAATCCCAGC ACTTTGGGAG GCCCAGATGG GTGGATCACC TGAGGTCAGG    540
AGTTCGAGAC CAGCCTGGAC AACATGGTGA AACCCTGTCT CTACTAAATA CTAAAGTTAG    600
CCCGGCATAG TGGCAGGTGC CTGTAATCCC AGCTACTTGG GAGGCTGAGG CAGGAGAATC    660
ACTTGAACCT GGGAGGTGGA GGTTGCAGTG AGCCGAGATC ACGACGCTGC ACTCCAGCCT    720
AGGTGACAGA GCAGGACTCT GTCTCAAAAA AAAAAAAAG TTATAGCACA GTCGACTCC     779
```

(2) INFORMATION FOR SEQ ID NO:24:

(i) SEQUENCE CHARACTERISTICS:
        (A) LENGTH: 526 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
    (B) CLONE: apDEL1, LOWER (xi) SEQUENCE DESCRIPTION: SEQ ID NO:24:

```
CTGGGCGTGG TGGCTCACAC CTGTAATCCC AGCACTTTGG GAGGCCGAGG TGGGTGGATC      60

ACCTGAGGTC AGGAGTTCAA GACCAGCCTG GCCAACATGG TGAAACCCCG TCTCTTAGCC     120

GGGCGTGGTG GCGCGCGCCT GTAATCCCAG CTACTCGGGA GGCTGAGGCA GGAGAATCGC     180

TTGAACCCAG GAGGTGGAGG TTGCAGTGAG CCGAGATCGC GCCACTGCAC TCCAGCCTGG     240

GCAACAGAGC GAGACTCCAT CTCCTGGGCG TGGTGGCTCA CACCTGTAAT CCCAGCACTT     300

TGGGAGGCCG AGGTGGGTGG ATCACCTGAG GTCAGGAGTT CAAGACCAGC CTGGCCAACA     360

TGGTGAAACC CCGTCTCTTA GCCGGGCGTG GTGGCGCGCG CCTGTAATCC CAGCTACTCG     420

GGAGGCTGAG GCAGGAGAAT CGCTTGAACC CAGGAGGTGG AGGTTGCAGT GAGCCGAGAT     480

CGCGCCACTG CACTCCAGCC TGGGCAACAG AGCGAGACTC CATCTC                    526
```

(2) INFORMATION FOR SEQ ID NO:25:

(i) SEQUENCE CHARACTERISTICS:
        (A) LENGTH: 427 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:25:

```
CAACTATTTC TAATTGTATA CAGCTAAATA TATGTGTATA TCTGGGTCTG AATATGTCTT      60

GGATATTTCT CGTTAATTTA TTTCATCTTG AAATACAAAA GTACAAAAGA AATATAAAAT     120

AGCCACTCAT CGGCCTGATG TGGTGGCTCA CGCTGTAATC CCAGCACTTT GGGAGGCCGA     180

GGTGGGCAGA TCATCAGGTC AAGAAATCGA GACCATCCTG GCCAACATGG TGAAATCCTG     240

TCTCTACTAA AAATACAAAA CTTAGCCAGG CATGGTGGTG CGTGCCTGTA GTCCCAACTA     300

CTCAGGAGGC TGAGGCAGAA GAATTGCTTG AACCTGGGAG TCAGAGGTTG CAGTGAGCCA     360

AGATCACGCC ATTGCACTCC AGCCTGGTGA CAGAGCCAGA CTCCGTCTCA AAAAAAAAA     420

GAAAAGA                                                                427
```

(2) INFORMATION FOR SEQ ID NO:26:

(i) SEQUENCE CHARACTERISTICS:
        (A) LENGTH: 283 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:26:

```
GGCTGGGCGT GGTGGCTCAC ACCTGTAATC CCAGCACTTT GGGAGGCCGA GGTGGGTGGA      60

TCACCTGAGG TCAGGAGTTC AAGACCAGCC TGGCCAACAT GGTGAAACCC CGTCTCTACT     120
```

-continued

| | | | | | |
|---|---|---|---|---|---|
| AAAAATACAA | AAATTAGCCG | GGCGTGGTGG | CGCGCGCCTG | TAATCCCAGC | TACTCGGGAG | 180 |
| GCTGAGGCAG | GAGAATCGCT | TGAACCCGGG | AGGTGGAGGT | TGCAGTGAGC | CGAGATCGCG | 240 |
| CCACTGCACT | CCAGCCTGGG | CGACAGAGCG | AGACTCCGTC | TCA | | 283 |

(2) INFORMATION FOR SEQ ID NO:27:

(i) SEQUENCE CHARACTERISTICS:
        (A) LENGTH: 440 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:27:

| | | | | | |
|---|---|---|---|---|---|
| GGAGTCGACT | GGTGCTATAA | CTTTTTTCCA | AATCAGTATA | AGAAAGGAAT | GATATCAAAA | 60 |
| AAAAAAAAAA | AAAAGGGAGT | GGGGAAAGAA | GGTGAGGTTG | GAAAGGAGAA | TTGTATCTAA | 120 |
| ACTCATAATT | TCTCCGTTTA | AGTTACTCAG | AATTGCCCGT | TGCGTTGTTA | AAGTGCAGAT | 180 |
| TGCTGGGCCT | CACTGTCTGA | TTCTGGGGAT | ATGGAGTGGG | CTCTTCTAAC | ATTTCTGAGC | 240 |
| TGCCACTGCT | GCTGGTTTGA | AAACCACACT | TTGAGAACCA | CCACTGTAGG | TAGAGTGGAG | 300 |
| ACCTCAGAGA | AGTCCAGTG | CTGTGCCAAA | GAGTTTGAGC | TTCACTCAAG | AGCAGCAGGG | 360 |
| AGACATTCAG | AGCTTGGTGA | AGAGGACGGT | GATAAGCTTC | TATGTACATA | TTAGGAGTCA | 420 |
| GAGCCAACCT | AGGACGTCAC | | | | | 440 |

IDENTIFICATION OF NEOPLASMS BY DETECTION OF GENETIC INSERTIONS AND DELETIONS

This application is a file wrapper continuation of U.S. patent application Ser. No. 08/152,484, filed Nov. 12, 1993, abandoned which was a continuation-in-part of U.S. patent application Ser. No. 07/975,737, filed Nov. 13, 1992 abandoned.

The invention is related to molecular methods for the diagnostic detection of neoplasms. It is particularly related to the identification of neoplastic cells and the characterization of tumors by determination of their genotypic properties.

BACKGROUND OF THE INVENTION

The somatic mutational theory of cancer (Knudson, 1971; 1985) has gained overwhelming support from the finding that mutations activate the malignant potential of oncogenes and inactivate the repressor function of tumor suppressor genes (Bishop, 1991). However, the etiology of these mutations remains poorly understood. There is no agreement on the estimation of the relative contribution by genotoxic agents and of spontaneous errors during DNA replication and repair to the genesis of these mutations in cancer. The importance of DNA replication and repair in malignant transformation is demonstrated by the association of various biochemical defects in these processes with hereditary diseases that predispose to cancer. The genes encoding protein factors involved in the DNA synthesis and repair pathways are beginning to be isolated and characterized. A causal link between defective factors involved in DNA metabolism and the origin of mutations in oncogenes and tumor suppressor genes is not yet in sight. The concept that spontaneous errors in the replication process may be fundamental in transformation was put forward in an attempt to explain the increased chromosomal alterations of cancer cells at late stages of tumor progression (Loeb et al., 1974). A defect in an enzyme involved in DNA replication could generate an enhanced rate of errors in the tumor cell variants continuously selected as tumor progression takes place (Foulds, 1954; Nowell, 1976). This defect could be therefore causative of the apparent genetic instability of malignant cells (Schimke et al., 1986). However, a critical prediction of this hypothesis, an increased mutation rate in tumor cells, has not been conclusively demonstrated despite intensive efforts (Harris, 1991; Loeb, 1991).

Hereditary diseases that predispose to cancer have also been associated with various biochemical defects in the processes of DNA replication and repair (Lindahl et al., 1991), implying that mutations in the genes encoding the protein factors involved in the DNA synthesis and error repair pathways could lead to malignant transformation. Again, however, no causal link between defective factors in DNA metabolism and the emergence of mutations in oncogenes has been established.

Colorectal cancer is one of the best characterized examples of the multistage nature of neoplastic development. A dominant oncogene, c-K-ras (Bos et al., 1987; Forrester et al., 1987) and at least three distinct tumor suppressor genes: p53 (Baker et al., 1989), DCC (Fearon et al., 1990), and MCC/APC (Kinzler et al., 1991a; 1991b; Groden et al., 1991) are consistently involved in colorectal tumorigenesis (Fearon and Vogelstein, 1990). In addition to the genetic alterations in these critical genes, other apparently random alterations in genome structure are observed in tumors of the colon and rectum, which exhibit remarkably heterogenous distribution in the extent of this genetic damage at the chromosomal level (Vogelstein et al., 1988; 1989).

Mutations corresponding to genetic alterations in tumor cells can comprise loss of heterozygosity (LOH) resulting from the loss of chromosomal sequences accompanying the inactivation of tumor suppressor genes, as well as increases in chromosomal sequences expressed in the aneuploidy of the cancer cell observed cytogenetically. In colorectal cancer, about 20% of the genomic sequences undergo losses of heterozygosity.

The search for genetic alterations that can be used for the detection of mutations associated with neoplastic change, either as deleted or amplified sequences, is complicated by the analytical requirements for analyzing closely related genetic sequences, the polymorphism among individuals, and the small amount of genetic material available for analysis.

DNA fingerprinting, based on polyacrylamide gel electrophoresis of labeled DNA restriction fragments, is a powerful technique for the comparative analysis of closely related genomes. It has been applied to the detection of polymorphisms during malignant transformation (Thein et al., 1987; de Jong et al., 1988), and to studies of the clonality of tumors, both primary and metastatic (Smit et al., 1988; Fey et al., 1988). DNA fingerprinting has been enhanced by its use in combination with the polymerase chain reaction (PCR) (Saiki et al., 1985; Mullis et al., 1987), which allows the reproducible amplification of primer-defined DNA sequences. A PCR-based DNA fingerprinting technique, called arbitrarily primed PCR, or AP-PCR (Welsh et al., 1990), utilizes amplification with a single arbitrary primer. The first cycles of amplification are performed at a low annealing temperature, which is raised in subsequent cycles to increase stringency. In the initial stages, the primer hybridizes to many sequences in the total genomic DNA. When the temperature is increased, only the best matches of the initial annealing events are amplified further, generating a number of discrete bands that provide a fingerprint of the cell genome. This approach has been used for mapping DNA polymorphisms in various prokaryotic and eukaryotic systems (Welsh et al., 1990; 1991). In a recent study, AP-PCR detected tumor-specific somatic genetic alterations by comparison of the fingerprints from normal and tumor tissue of the same individual. Cloning and analysis of the altered DNA bands from tumors of the colon and rectum (Peinado et al., 1992) determined that somatic deletions of a few nucleotides had occurred in a subset of colon tumors.

It is therefore an object of the invention to provide methods based on DNA fingerprinting and auxiliary amplification techniques, such as PCR, that can be used to identify genetic alterations that are predictive or diagnostic of neoplastic change in cells.

It is another object of the invention to provide a method for the diagnostic identification of a particular class of tumors based on the presence of these mutations.

It is yet another object of the invention to provide a method for the molecular diagnosis of tumors that have predictive value of malignant transformation.

It is yet another object of the invention to provide a simple diagnostic method for the molecular diagnosis of tumors that have predictive value for cancer prognosis.

SUMMARY OF THE INVENTION

The invention provides a method for identifying tumors comprising the steps of obtaining tissue or sample DNA from a potential tumor, and analyzing DNA or RNA of the sample from at least one genomic region typically containing reiterated sequences to determine whether insertion or deletion mutations have occurred in the reiterated sequences.

In a preferred embodiment, the method of the present invention utilizes amplification by PCR of tumor tissue DNA. According to preferred protocols, the PCR amplification procedures are carried out so that at least two different genomic regions containing reiterated sequences are amplified.

In these protocols, the amplification includes the step of contacting the sample DNA with a first set of primers adapted to amplify a first region thereof containing reiterated sequences, and contacting the sample DNA with a second pair of primers adapted to amplify a second region thereof containing reiterated sequences. In another embodiment, the method of amplification is arbitrarily-primed PCR amplification. In an alternative embodiment, the amplification is ligase chain reaction amplification.

In a particularly preferred embodiment of the invention, amplification only occurs if insertions or deletions in the region have occurred. In preferred protocols related to this aspect of the invention also, the amplification step can comprise contacting the DNA with a first set of primers complementary to sequences flanking the reiterated sequences, amplification of the region occurring only if a first number of insertions or deletions has occurred, and a second set of primers complementary to sequences flanking the reiterated sequences, amplification of the region occurring only if a different, second number of insertions or deletions has occurred. The preferred protocol the amplification step can comprise contacting the DNA with a third set of primers complementary to sequences flanking the reiterated sequences, amplification of the region occurring only if a third number of insertions or deletions has occurred, wherein the third number is different from the first and second numbers.

In an alternative embodiment of the invention, there is provided a method for identifying tumor cells comprising the steps of (a) obtaining a sample containing DNA from a potential tumor, (b) contacting the sample with primers that are complementary to a predetermined portion of the DNA which typically contains reiterated sequences, (c) subjecting the sample and the primers to amplification steps to amplify such DNA, and (d) determining whether amplification of DNA occurs, wherein amplification indicates the presence of tumor cells. In a preferred embodiment, the method further comprises the steps of performing a control assay by also obtaining control sample containing DNA from normal tissue, subjecting the control sample to steps (b) through (d), above. In a particularly preferred embodiment, the control sample and the tumor sample are obtained from a common patient. In a most preferred embodiment of the invention, amplification occurs only when insertions or deletions have occurred.

According to another particularly preferred embodiment, the test for inserted or deleted sequences is carried out by the Southern hybridization method.

The invention also provides a diagnostic kit to identify tumor cells, comprising a compartmented enclosure containing at least one set of primer pairs complementary to a predetermined portion of DNA from the tumor cells which ordinarily contain reiterated sequences, and reagents to carry out PCR amplification, and optionally, control DNA sequence samples, a polyacrylamide gel slab, and electrophoresis buffer. The invention also includes a diagnostic kit adapted to identify insertion or deletion-associated neoplasms by use of the ligase chain reaction (LCR) process comprising a first pair of ligase chain reaction primers complementary to a predetermined region of DNA which ordinarily contains reiterated sequences, amplification occurring only if one or more insertions or deletions have occurred in a reiterated sequence contained within said region; and reagents for performing ligase chain reaction using said primers. In a preferred embodiment of this aspect of the invention, the kit further comprises a second pair of primers adapted to amplify said region only if a different, second number of insertions or deletions have occurred in the reiterated sequence. In yet another preferred embodiment of this aspect of the invention, the kit further comprises a third pair of primers adapted to amplify said region only if a third number of insertions or deletions have occurred in said reiterated sequence, wherein the third number is different from the first and second numbers.

BRIEF DESCRIPTION OF THE DRAWINGS

FIG. 3 represents the nucleotide sequence of APΔ1 and the binding sites of the arbitrary primers used to amplify the sequence.

FIG. 4 represents the nucleotide sequence of APΔ2 and the binding sites of the arbitrary primers used to amplify the sequence.

FIG. 5 represents the nucleotide sequence of APΔ3 and the binding sites of the arbitrary primers used to amplify the sequence.

DETAILED DESCRIPTION OF THE INVENTION

The present invention provides a method for the molecular diagnosis of genetic alterations that are associated with a significant group of human cancers based on the presence of ubiquitous somatic mutations (USM) in the tumor cell genome. These mutations are deletions or insertions of one or a few nucleotides in genomic sequences containing simple repeated sequences (SRS) or repetitive microsatellite DNA sequences. Detection of these somatic alterations can be utilized as a tool for cancer diagnosis and prognosis.

We have found that the genome in many types of neoplastic cells contain hundreds of thousands, and in some cases up to a million, of DNA sequences having deletions or insertions of a few nucleotides in simple repeated sequences, usually monotonic runs of base pairs as well as dinucleotide and trinucleotide simple repeats. The presence of ubiquitous USM in this group of tumors suggests a previously unrecognized molecular genetic pathway for neoplastic change, one that involves a catastrophic subversion of the mechanisms responsible for the fidelity of DNA replication of unstable repeated sequences. This mechanism may involve the mutational activation of a mutator gene (a gene coding for a replication or repair factor which, when mutated, leads to a decreased fidelity of replication and/or repair), resulting in the accumulation of USM in SRS.

Site and Characteristics of the Mutations

As used herein, a "reiterated sequence" means a nucleotide sequence containing runs, that is, multiple adjacent occurrences, of the same nucleotide, dinucleotide pair, or nucleotide triplet.

Figure 6:
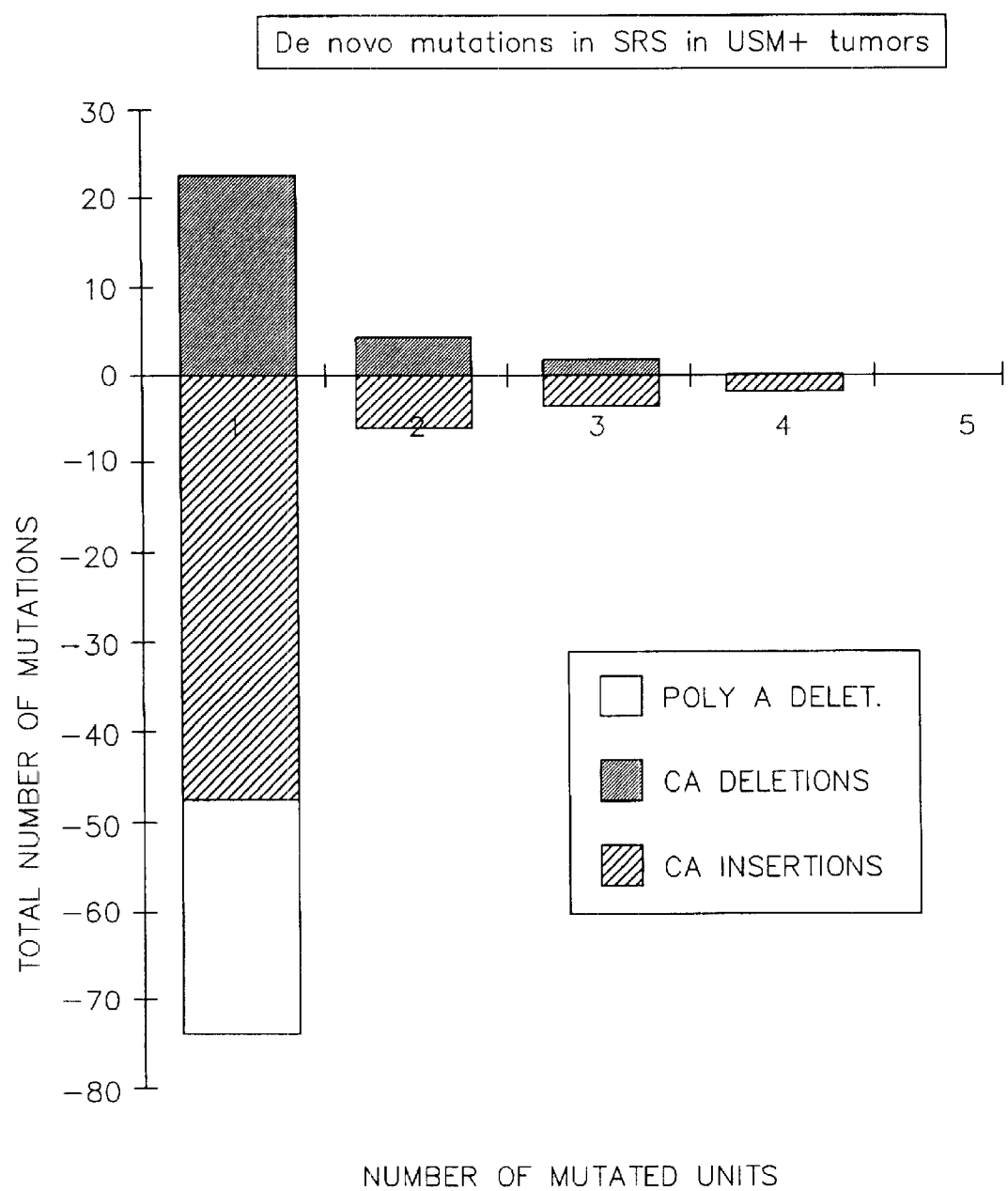
FIG. 6 represents the frequency of de novo mutations in simple repeated sequences in USM+ tumors.

As used herein, the term "microsatellite" refers to a short (1–6 base pair) tandemly repeated DNA sequence and the term "mutation" refers to insertions or deletions of one or a few base pairs in simple repeated sequences. The reiterative sequences target for the deletion or insertion mutations can be monotonic runs of dA:dT or dC:dG base pairs (AAAAAAAAA, GGGGGGG), any of the possible dinucleotide repeats such as CA/GT, CT/GA, or TA/AT (CACACACA, CTCTCTCT, TATATATA) or trinucleotide repeats such as AAT, AAG, AAC, CAA, CAT, GGT, GGC, or the like. Monotonic runs of As undergo preferentially deletions, while di- and trinucleotide repeats also undergo insertions. The most prevalent site for the deletions appears to be the poly(A) tails of the Alu repeats. CT/GA repeats appear to contain more deletions than insertions, while CA/GT repeats appear to contain more insertions than deletions (FIG. 6). The somatic instability of colorectal tumor DNA at CA repeats has also been demonstrated by both Thibodeau et al., (1993) and Aaltonen et al., (1993). Although the maximum size of the repeat that is subject to these deletions or insertions is unclear, the mutation rate appears to decrease with the number of nucleotides in the repeat. That is, runs of A's have higher mutation rates than dinucleotide repeats, and these have rates higher than trinucleotide repeats, and so forth (AAAAAAAAAAAA>CACACACACACA>GGTGGTG-GTGGT). Some data indicate there may be a functional limit in the size of the repeat beyond which deletions or insertions of this type will not occur.

The mutation rate, and therefore the probability of finding a deletion or insertion in a particular sequence in the DNA of a tumor cell is also related to the length of the repeat. For example, a run of 30 dA:dT bp will almost certainly have undergone deletions in these tumors; a sequence with only 20 dA:dT bp will have undergone deletions in the majority of the tumors. A run of 10 dA:dT or less will be found to have undergone deletions only in some tumors having mutations in the longer repeats.

Methods of Detecting USM in SRS

The detection of tumor specific insertion or deletion mutations can be achieved by a number of molecular methods, preferably methods based on the polymerase chain reaction (PCR) using complementary primers flanking any one of the multiple repetitive genomic sequences that undergo this type of mutation. Other amplification based methods that can be used include the arbitrarily primed PCR (AP-PCR), the ligase chain reaction (LCR), amplification by reverse transcriptase, or any other method based on cycling enzymatic reactions of genomic DNA or RNA sequences. These deletion and insertion mutations can also be detected by non-PCR methods, such as Southern blots (Example 6) and RNase A mismatch cleavage (Winter et al., 1985; Example 7), although such methods are more technically difficult.

The general scheme of identifying and characterizing the mutations comprises (1) an identification of gene fragments in which structural genetic alterations occur by DNA fingerprinting, usually facilitated by PCR based amplification; (2) amplification of the insertion or deletion bearing fragments; and (3) detection of the sequence bearing insertions or deletions. The procedures may be supplemented by cloning and sequencing.

1. Amplification by AP-PCR

Arbitrarily-primed (AP) PCR is a DNA fingerprinting technique based on the in vitro amplification of multiple genomic DNA fragments by the use of single PCR primers having arbitrarily chosen nucleotide sequences (Welsh and McClelland, 1990). A similar method also using arbitrary primers has been described (Williams et al., 1990). The experiment is begun at a low annealing temperature initially, and then the temperature is raised to increase the stringency during the enzymatic cycling. Competition among the best matches of the initial successful annealing events, during the subsequent high stringency cycles, results in the amplification of 25–100 discrete bands. Under appropriately controlled conditions, the method produces highly quantitative, reproducible amplification that is independent to a great extent of the concentration of the target DNA sequences. The method has been successful in the fingerprinting and mapping of DNA polymorphisms in prokaryotes (Welsh and McClelland, 1990) and eukaryotes (Welsh et al., 1991), and in the detection and characterization of quantitative genetic alterations during tumorigenesis (Peinado et al, 1992). In addition to these quantitative alterations, AP-PCR permitted the identification of qualitative alterations, resulting in the presence in some tumors of USM in SRS or microsatellites which, upon AP-PCR amplification, showed different mobilities on acrylamide gels. Since the primers are random, and no one primer is particularly advantageous over another, a large number may be used to detect mutations in microsatellite sequences accurately and reproducibly.

Figure 7:
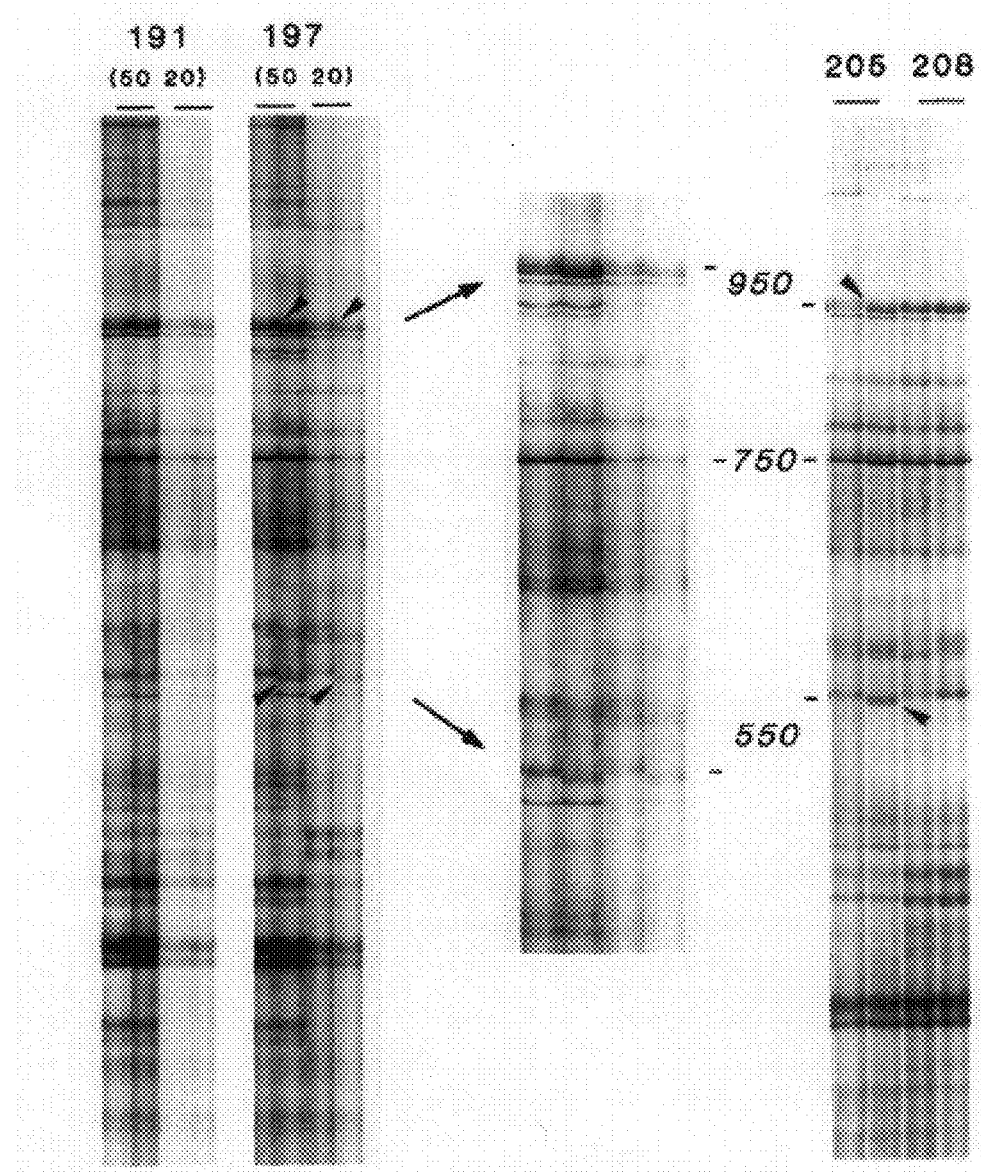
FIG. 7 represents an autoradiogram of AP-PCR fingerprints of matched pair normal-tumor tissue DNAs from colorectal carcinomas obtained with the arbitrary F primer (KPNX). Numbers on top indicate the case number. Normal and tumor tissues (left and right, respectively) were analyzed using two different DNA concentrations (50 and 20 ng). The arrowheads indicate shifts in band mobility. The numbers inside indicate the molecular weight (in nucleotides) of some bands. A higher magnification of case 197 is shown in the center. The AP-PCR $^{32}$P-labeled products were diluted 1:1 with formamide loading buffer, denatured at 90° C. for 3 minutes and analyzed on a 6% polyacrylamide gel containing 8 M urea.

Example 1 describes in detail the AP-PCR protocol and its application to samples of tissue to matched normal-tumor DNA samples from colorectal cancer patients. Differences in the mobilities of bands were suggestive of somatic mutations because they were tumor specific. In a study of a panel of 4 pairs of matched normal-tumor DNA samples from colorectal cancer patients (Nos. 197, 191, 205 and 208), alterations in the mobilities of bands of 950 and 550 nt were observed in tumor relative to normal tissue DNA in cases 197 and 205. The tumor-specific bands showed an apparently slightly smaller size in both tumors (FIG. 7). In contrast, no alterations in the mobility of these bands were observed in tumors 191 and 208. The same results were observed with other tumors analyzed with the same arbitrary primer. In all cases, the tumor tissue bands migrated faster than the normal tissue bands, suggesting that in these tumors, small deletions had occurred in some of the genomic sequences amplified by PCR. Furthermore, when polymorphic microsatellite DNA sequences containing CT repeats were amplified by PCR, insertions, as well as deletions, were observed (Example 2).

The mobility alteration phenomenon was not restricted to the arbitrary F primer used in the experiment of FIG. 7, but also was observed with other primers. AP-PCR patterns obtained with unrelated primers, of normal and tumor tissue DNAs from cases 197 and 91, also showed altered patterns of bands with the F primer. Alterations in the migration of bands were observed with primer B (bands of 750 and 450 nt) and with the combinations of primers B+C (an additional band of 550 nt). No alterations in band mobilities were detected with primers A, C, or A+B (Ionov et al., 1993). Six out of ten of the arbitrary primers used generated AP-PCR patterns with alterations in the mobility of at least one band. Without exception, the alterations showed an apparent reduction in the size of the bands in tumor tissue.

Determining the Nature of Sequence Alterations by Cloning and Sequencing

The nature of the alterations in the gene fragments having altered mobility can be determined by cloning and sequencing as set forth in Example 1. The 750 nt polymorphic band of the tissue from case 91 (Ionov et al., 1993) was cloned and the nucleotide sequence of the cloned DNA fragments (APΔ1) from normal and tumor tissue was determined. A DNA fragment comprising the 550 nt band amplified with primer F (APΔ2) (FIG. 7) was also cloned and sequenced. Both fragments contained Alu repeats, APΔ1 having two Alu repeats in a head to tail array, and APΔ2 having a single Alu repeat. The sequencing data suggested that in both APΔ1 and APΔ2, the poly(A) tails of the Alu repeats were shorter in the tumor than in the normal tissue DNA. The sequence information of cloned APΔ2 DNA fragments was used to determine their nucleotide sequences directly from genomic DNA by cycle sequencing after their amplification by PCR, as described in Example 1. All tumors with apparent deletions previously identified by AP-PCR contained shorter runs of deoxyadenines in the poly(A) tails of the Alu repeats relative to their corresponding normal tissues. These apparent deletions also occurred in runs of dA:dT base pairs present in other DNA sequences that did not contain Alu repeats. The band of 550 nt amplified with the combination of primers B+C is an example (Ionov et al., 1993). The sequence of this cloned DNA fragment (APΔ3) revealed the absence of Alu or any other repetitive sequences. The nucleotide sequences of the AP-PCR amplified bands from normal and tumor tissue DNA from case 197 were analyzed. The normal tissue DNA contained a run of about 17 thymidines, while the tumor tissue DNA contained about 13 thymidines.

To determine more accurately the length of the monotonic runs of dA:dT base pairs in these sequences, and their differences between normal and tumor tissue, the APΔ3 DNA fragments were cloned in several independent plasmids after AP-PCR amplification from both normal and tumor tissue from patient 197, and the cloned fragment was then sequenced. The heterozygosity status of APΔ3 sequences did not represent a problem in this case because they were localized on chromosome X and patient 197 was a male. The chromosomal localization of these sequences was determined by PCR using panels of human/rodent cell hybrids, comprising the PCR amplifiable panel from Bio (New Haven, Conn.) and the NIGMS mapping panel II from Coriell Institute for Medical Research (Camden, N.J.), and the APΔ3U and APΔ3D primers. The nucleotide sequences of two plasmids from normal tissue and one from tumor tissue were analyzed according to Example 1. The lengths of the runs of deoxyadenines in these plasmids were 16 and 18 for the normal tissue and 14 for the tumor tissue. The distribution of the length of these repeats in the plasmids is shown in Table 1. As predicted by the diffuse bands of the sequencing ladders, the runs of dA:dT base pairs in APΔ3 sequences appeared heterogenous in both normal and tumor tissues. While the normal tissue DNA contained an average of 17.3 deoxyadenines, the average size in the tumor tissue DNA was 13. In agreement with the sequencing of genomic sequences, these results show that a deletion of about 4 nucleotides had occurred in APΔ3 sequences in these tumor cells. The length heterogeneity of these sequences was not due to their instability during propagation in *E. coli* because sequencing of 8 different plasmids obtained by transfection of *E. coli* with the plasmid of 18 deoxyadenines revealed no differences in this number of nucleotides.

A comparison of APΔ3 PCR products obtained from genomic DNA with those obtained from cloned DNA showed band patterns that were indistinguishable from patterns resulting from single plasmids containing 14 and 18 dA:dT pairs, respectively. Because the population of plasmid molecules was at least 80% homogenous, the results indicated that these sequences were equally homogenous in the tissues.

The somatic deletion mutations were ubiquitous in colorectal carcinomas. Amplification by standard PCR of APΔ2 and APΔ3 DNA sequences of normal/tumor DNAs showed bands in both sequences a few nucleotides smaller than those corresponding to the normal tissue DNA in eight of ten cases. The detection of somatic deletions in sequences amplified by AP-PCR implied that these mutations were generalized in the genome of these colorectal tumors, because of the random origin of the AP-PCR bands due to the arbitrary nature of the primer sequences. The presence of deletions in several independent Alu repeats added support to the concept that they were ubiquitous in the tumor genome.

Linkage of Somatic Deletions to Pathological Conditions

The occurrence of base deletions in the nucleotide sequences of tumor cells is characteristic of a disease process in these cells, and was not found to be an artifact or consequence of heterogeneity. It has been experimentally determined that the length heterogeneity in poly dA:dT sequences shown by the diffuse bands above the strings of deoxyadenines were not due to tissue heterogeneity, but rather to Taq polymerase errors. A similar conclusion has been reached for the apparent heterogeneity of C-A repeats after PCR amplification (Weber and May, 1989). Experimental studies also showed that the APΔ3 sequences predominantly present in the normal tissue cells contained 18 deoxyadenines, while the sequences from the tumor cells contained only 14. Therefore, these results demonstrate that a somatic deletion of 4 base pairs had occurred in the APΔ3 sequences in cells from colorectal carcinoma 197, and that the apparent length diversity in these repeated sequences was not due to tissue cell heterogeneity.

Further, there is an ubiquitous presence of somatic deletion mutations in colorectal carcinomas. When APΔ2 and APΔ3 DNA sequences from pairs of normal/tumor DNAs were amplified by standard PCR, no difference was observed in the mobility of bands from tumor versus normal tissues of cases 78 and 83; in all other cases, the band corresponding to tumor tissue DNA was present in both APΔ2 and APΔ3 sequences, a few nucleotide bases smaller than those corresponding to their normal tissue DNA. The presence of deletions in several independent Alu repeats added support to the concept that they were ubiquitous in the tumor cell genome. Other experiments showed that deletions occur in many other sequences containing runs of deoxyadenine of equivalent size to those present in APΔ2 and APΔ3.

Further, the genomic sequences having deletions were shown to be clonal and homogenous within tumors. In some tumors, both wild type and mutant bands were present (cases 91, 149 and 238); however, in many cases, the bands of normal size were absent, or present in a minor proportion in the tumor tissue DNA. The absence of wild type alleles implied that the mutant alleles were present in most, if not all of the tumor cells; therefore the deletions appear to be clonal.

Other experimental work has shown that these ubiquitous somatic deletions are clustered in a subset of colorectal carcinomas. Of 137 colorectal carcinomas analyzed for the presence of deletions in the APΔ3 sequences by standard PCR, 16 were found positive. In all 16 tumors with deletions in the APΔ3 sequences, there were also deletions in the other two sequences, with a single exception, which did not have deletions in the Alu sequence. On the other hand, all tumors negative for deletions in one DNA fragment, were also negative for deletions in the others. The apparent clustering of mutations in these tumors suggested that these deletions occurred only in some colorectal cancers. However, these mutations could also occur in all or at least in some other tumors, while only those tumors with the highest number of mutations were detected with the few primers utilized. In an effort to distinguish between these two possibilities, 74 of the carcinomas analyzed for the APΔ3 sequences were also analyzed by PCR with the Alu J primer. This experiment was intended to increase the number of deletions detectable in a single experiment, because using high stringency conditions, most of the amplified bands should contain repeated Alu sequences (Sinnet et al., 1990). This approach generated DNA fingerprints with apparent deletions in multiple bands. In some of the positive cases, about one third of the amplified DNA fragments showed increased mobility. This value is probably an underestimation, because deletions of only one or two nucleotides would not be detectable in the bands of high molecular weight. All positive tumors for deletions in APΔ2, APΔ3, and c-K-ras Alu sequences also yielded apparent deletions in the Alu PCR band pattern. In contrast, none of the tumors previously found negative for deletions in these three sequences exhibited noticeable deletions in the Alu PCR bands.

Figure 1:
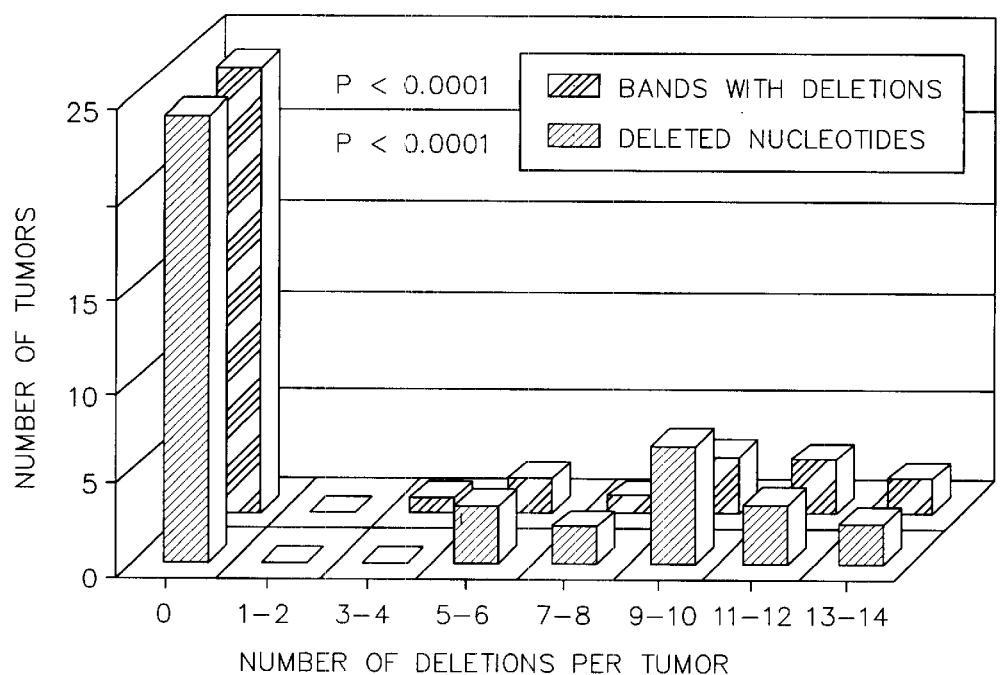
FIG. 1 is a graphical representation of the total number of deleted nucleotides in the APΔ2, APΔ3, and c-K-ras Alu sequences from colorectal carcinomas and the total number of bands with deletions after PCR analysis of these three DNA sequences plus those observed by Alu PCR with primer J.
Figure 2:
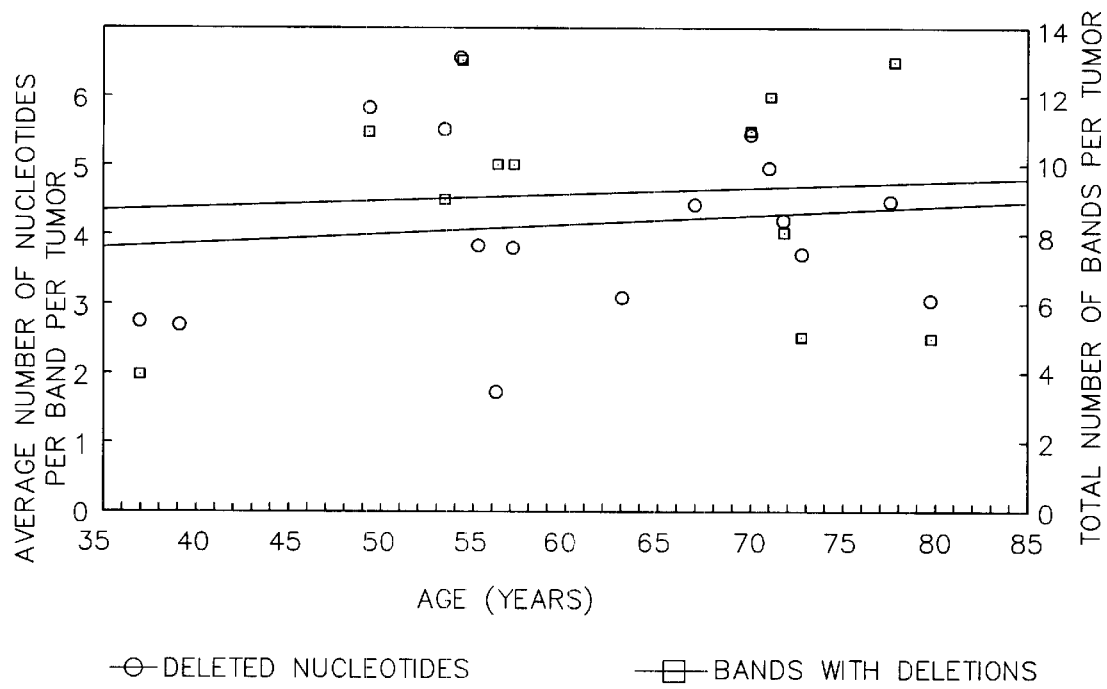
FIG. 2 is a graphical representation of the distribution of the corrected average number of base pairs in the APΔ2, APΔ3, and Alu c-K-ras DNA bands from colorectal tumors, and the total number of bands with deletions per tumor, plotted according to the age of the colorectal cancer patients.

A test for deviation of the Poisson distribution by these mutations indicated that they were significantly clustered in the same colorectal carcinomas, whether the calculations were made using the total number of bands with deletions, or the total number of deleted nucleotides in the APΔ2, APΔ3 and c-K-ras sequences (FIG. 1). The mutations were also found to be independent of the age of the cancer patients and therefore they are not the result of the steady accumulation of errors during aging (FIG. 2). Therefore, the detection of these somatic deletions in only some tumors cannot be explained by a random distribution of mutations in all colorectal cancers, with only those with the highest number of mutations detectable with a few primers.

Detection of USM in Other Dinucleotide and Trinucleotide Repeated Sequences or Microsatellites Tumors with USM in poly A sequences also contained mutations in other simple tandemly repeated sequences or microsatellites. Alterations in the length of CA and CT dinucleotide and of CAG trinucleotide repeated sequences were detected by standard PCR amplification of several polymorphic microsatellite sequences using specific PCR primers available for gene mapping from several commercial sources, including the Map Pairs from Research Genetics, Huntsville, Ala. Alterations in the length of these microsatellite sequences were present in the subset of tumors with USM in poly A sequences (Ionov et al, 1993). The alterations were found to consist of both insertions and deletions of one or a few dinucleotides in the CT and CA repeats (FIG. 8), and of one or a few trinucleotides in the CAG repeats.

Utility of the Identification of Deletions in Clinical Medicine

The timing of occurrence of these somatic mutations during colorectal tumorigenesis is not known. Their clonal nature suggests that they occur before malignant transformation. The presence of these mutations in colorectal adenomas, benign tumors which progress to carcinomas, also demonstrated that these mutations are early events in colorectal cancer (Ionov et al, 1993), and in that sense, they are believed to be predictive of malignant change.

The neoplasms in which these USM in SRS occur have distinctive genotypic, phenotypic, and clinical properties (Table 2). Tumors with generalized deletions in poly A sequences and deletions and insertions in di- and trinucleotide microsatellite sequences correlated positively with tumors exhibiting a poorly differentiated phenotype, with tumors of the proximal colon, and with tumors of African-Americans. They also appeared to be associated with an early onset for cancer. On the other hand, these mutations correlated negatively with mutations in the p53 tumor suppressor and c-K-ras genes and with tumors that had metastasized at diagnosis. The generalized genomic alterations occurred more frequently in tumors with no metastasis than in tumors with detectable metastasis at diagnosis, and no deletion mutations were found in 19 metastatic tumors. Furthermore, tumors with USM in SRS exhibited a lower rate of recurrence than tumors without USM in SRS (Table 2), indicating another important diagnostic application for the identification of these deleted sequences. Thus, the identification of tumors having USM in SRS by the method of the present invention will be useful in determining the course of treatment for these tumors.

In addition to 12% of the colorectal tumors, these USM in SRS have also been observed in about 10% of stomach and pancreatic cancers. Cancers of the lung and kidney appear so far to be negative. The deletions occurred in 22 of about 170 tumors of the colon, including 2 benign adenomas. Four of these tumors, two carcinomas and the two adenomas, were present in the same patient, suggesting strongly that these deletions are facilitated by a genetic predisposition. The identification of mutations in SRS can then be used to screen the population for this predisposition, which is very likely a germ line mutation in a gene involved in DNA synthesis or repair. The USM in SRS are the phenotypic molecular manifestations of a hereditary and familial cancer syndrome (Lynch Syndrome I and II). Accordingly, the diagnostic detection of these USM in SRS has direct applications for predicting the risk of cancer in family members of affected patients. For instance, brother and sisters of a colorectal cancer patient with USM in SRS tumor, are at higher risk to develop colorectal cancer than the rest of the population. Thus, USM in SRS in tumor cells are associated with distinctive characteristics in genotypic, phenotypic, anatomical, ethnic, biological and clinical parameters. The tumors having these deletions have a different behavior, and a different prognosis, in that they appear to be less invasive than other tumors and may recur less frequently. For these reasons, the ability to identify somatic mutations in microsatellite sequences represents a valuable diagnostic application having great significance with respect to prognosis and the chosen course of therapy.

Diagnostic Applications and Reagents

A diagnostic protocol for screening or evaluation of tumor status preferably should initially identify a long SRS in the tumor cell. That sequence can then be analyzed for the presence of deletions or insertions in reference to a control sample of normal tissue. The analysis can proceed through the amplification and analytical steps described above and used in identifying and characterizing mutations in the repeating DNA sequences of the cells of colon or other tumors. Using analytical methods based on PCR or LCR, or other methods as set forth in Examples 1–4, 7, 8, and a number of primers, analysis can be performed with as little as 20 nanograms of total genomic DNA prepared from tumor specimens. Ideally, normal tissue from the same individual is also analyzed, although this is not absolutely necessary. In this way, it can be determined if the tumor analyzed belongs to the class of tumors containing an enormous number of these mutations in the genome. Finding, for instance, a deletion in one or preferably, in two or three of the sequences analyzed can be immediately extrapolated to the presence in the tumor of hundreds of thousands of similar mutations. The determination is particularly useful because the data presented herein indicates that tumors with these generalized mutations exhibit distinct properties that distinguish them from other tumors.

The analysis for insertions or deletions can be carried out with great specificity to indicate not only the nucleotide sequences wherein these mutations have occurred but the pattern of mutation, in terms of the number of regions of the DNA wherein insertions or deletions have occurred, and whether single, double, or multiple reiterated insertions or deletions have occurred singly or in combination. These mutation patterns can be constructed by using sets of specific primer pairs, first in the amplification of reiterated sequences, and then using other sets of specific primer pairs in the amplification of reiterated sequences in which mutations have occurred. In the amplification of reiterated sequences, the primer pairs can be, for example, those pairs adapted to amplify each distinct region containing reiterated sequences, and thus subject to the mutations described above. In the amplification of inserted or deleted sequences, the primer pairs can be, for example, those pairs adapted to determine precise numbers of inserted or deleted nucleotides in the regions containing reiterated sequences, such as single, double, or multiple mutations in each amplified reiterated sequence.

There are a variety of kit formats known in the art that can be used to generate suitable diagnostic kits in accordance with the present invention. These kits are based on the knowledge of the nucleic acid sequences identified for the deletion-associated tumors. Example 1 below discloses the AP-PCR method suitable for identifying the nucleic acid fragments containing deletion associated sequences. Those with skill in the art of molecular biology will be readily able to modify the AP-PCR primers to include restriction endonuclease cleavage sites or the like and to generate nucleic acid fragments containing the deletion/insertion-associated sequences that can be readily cloned into suitable vectors adaptable for DNA sequencing. An example of a method for obtaining nucleic acid fragments containing the deletion/insertion-associated sequences and generating the nucleic acid sequence therefrom is provided in Example 3.

Those interested in developing kits for the diagnosis and identification of deletion/insertion-associated tumors can easily assess the frequency of a given mutation present in a deletion/insertion-associated sequence within the population without undue experimentation. Studies provided herein indicate that APΔ1, APΔ2 and APΔ3 are deletion-associated sequences where deletions are likely to occur in deletion-associated tumors.

Therefore in one example kits for the identification of deletion-associated tumors are generated based on the normal and deleted sequences of APΔ2 and APΔ3. As one example of a kit strategy, it is contemplated that a ligase chain reaction (LCR) kit is prepared based on the APΔ2–3 sequences. Example 4 provides an exemplary strategy for developing a ligase chain reaction kit.

The LCR kit is designed such that a deletion-associated cancer produces a positive result. Primers from these high-frequency sequences are prepared by synthetic oligonucleotide synthesis methods, well known in the art. The LCR reaction uses labelled primers representing at least two high-frequency sequences. In this embodiment, the amplified ligated sequence is derived from primers that represent those specific regions from the sample nucleic acid that contain the deletions. A positive signal indicates the presence of a deletion-associated tumor.

Example 1 provides PCR primers that amplify APΔ1–3 from normal and tumor tissue. These primers are useful in any number of PCR related diagnostic tests. These tests preferably include the primer pairs, suitable reagent mixtures (10× concentrations of the reagents provided in Example 4) and Taq polymerase. The clinician supplies the thermocycler or the water baths set at the preferred cycling temperatures. Example 4 provides a PCR strategy suitable for generating USM in SRS-associated sequences from normal and tumorigenic tissue. The amplified fragments are separated by gel electrophoresis and differentiated by size. Deletion-associated sequences will migrate faster on the electrophoretic gel. Insertion-associated sequences will migrate slower on the gel.

Sequences useful as targets for detection of USM in these tumors may also be obtained from the collection of microsatellite sequences presently available from a number of commercial sources, including Research Genetics, Huntsville, Ala., originally isolated and designed for mapping purposes (Weber and May, 1989; Weber, 1990; Weber and Wong, 1993; Beckman and Weber, 1992; Hearne et al., 1992; Hudson et al., 1992). Any of these polymorphic microsatellite sequences can be used for diagnostic tests because of the very high probability of having undergone deletions or insertions in the genome of the tumor cells with the USM in SRS phenotype.

It is also contemplated within the scope of this invention that labeled probes (either normal probes or deletion/ insertion-containing probes) complementary to the internal portion of the sequence can additionally be used to verify the presence of mutations in SRS.

As an alternative method for the detection of insertion or deletion-associated sequences and insertion or deletion-associated tumors, it is contemplated that a Southern hybridization method is developed as a diagnostic kit either in an gel electrophoretic format or as a dot blot. Preferably the hybridization conditions are designed to adequately differentiate between sequences that contain deletions/insertions as compared to the normal sequence. Example 6 provides a Southern hybridization method using tetramethyl ammonium chloride (TMAC). In this example, the detection of deletion/insertion-associated tumors does not depend on the identification of deletions/insertions contained within the deletion/insertion-associated sequence. Instead, the assay depends on the normal counterpart of a deletion/insertion-associated sequence. In one embodiment of this method PCR is used to amplify the deletion-associated sequences from the genomic background, and in another example a biopsy of sufficient size is obtained such that 5–10 μg of DNA is available for each spot of a dot blot. The DNA obtained from the normal and tumor tissue is blotted onto nitrocellulose or another suitable hybridization membrane and the DNA is hybridized with a probe corresponding to a high-frequency deletion region within a deletion-associated sequence that is exactly complementary to normal tissue. Following hybridization, the probe is successively washed in increasing temperatures using the wash buffer provided in Example 6. As the melting temperature of the probe to its complementary sequence is approached, the probe will wash away from sequences that are not exactly complementary. Therefore successive washes and exposure of the blot to autoradiography will result in the disappearance of a radioactive signal with increasing temperature in deletion-associated tumor DNA while normal DNA will still generate a positive signal until the melting temperature of the probe and DNA is reached. Protocols for TMAC hybridization and the melting temperatures corresponding to different probe lengths are available in Current Protocols in Molecular Biology (Ausubel et al., eds, 1989).

Other characteristics and advantages of the invention are more clearly demonstrated by the following examples, which are of course only illustrations, and not intended to be exhaustive.

EXAMPLE 1

AP-PCR to Identify Deletions in Sequences of DNA from Tumorigenic Tissue

A panel of 139 paired samples of tumor tissue and normal tissue from the same patient were processed to isolate genomic DNA using the methods disclosed by Nakano, et al. (1984) *Proc. Natl. Acad. Sci. USA* 81:71–75. Normal and tumor tissues were analyzed using two different DNA concentrations (50 and 20 ng). AP-PCR reactions were performed with 125 μm of each deoxynucleotide, 2 μm arbitrary primers, 5 μCi α-$^{35}$S-dATP or 1 μCi α-$^{32}$P-dCTP (New England Nuclear, Boston, Mass.) and 2 units of Taq polymerase (Cetus/Perkin Elmer or Stratagene) in the PCR buffer disclosed in Example 4 below. The arbitrary primers used to identify the deletion-associated sequences are listed as sequences A through J below. The reaction consisted of 5 low-stringency cycles (usually 1 minute at 95° C., 1 minute at 50° C., 1.5 minutes at 72° C.) and 30 high stringency cycles (usually 30 seconds at 95° C., 30 seconds at 60° C., 1.5 minutes at 72° C.). The AP-PCR $^{32}$P-labeled products were diluted 1:1 with formamide-loading buffer, denatured at 90° C. for 3 minutes and analyzed on a 6% acrylamide, 8 M urea sequencing gel. The size of the nucleotide bands was estimated by means of Φ×174 restriction fragments run as markers. The results indicated that the tumors in cases 197 and 205 exhibited deletions since DNA fragments were observed which migrated faster on the gel than did their normal counterparts (FIG. 7).

The arbitrary primers used in this study are listed below. At right is indicated whether the primer did (+) or did not (−) yield bands with deletions (combinations of primers in parenthesis). Increasing signs (+) denote number of g\bands with deletions: one(+); two(++); more than two (+++); deletions detected in only some of the tumors with deletions detected with other primers (+/−); N: not analyzed. At least 40 matched normal/tumor DNA pairs were analyzed with each primer or combination of primers. A=SEQ ID NO: 1; B=SEQ ID NO: 2; C=SEQ ID NO: 3; D=SEQ ID NO: 4; E=SEQ ID NO: 5; F=SEQ ID NO:6; G=SEQ ID NO: 7; H=SEQ ID NO: 8; I=SEQ ID NO: 9; J=SEQ ID NO: 10.

```
A (3U)    5' AAGGGATCCCCCTTGCCGTCC 3'          -
B (K3US)  5' GGAGTCGACTGGTGCTATAACTTTTTT 3'    ++
C (6U):   5' GTGAGCTCCTAGGTTGGCTCTGACT 3'      - (+ B/C)
D (8D):   5' CTGAAGGGTGAAATATTCCTCC 3'         +
E (10DN): 5' ATGGCGGGAGGTGACTGAC 3'            N (- A/E)
F (KpnX): 5' CTTGCGGGAGGTGACTGAC 3'            ++
G (MCG1): 5' AACCCTCACCCTAACCCCAA 3'           +/-
H (LH1):  5' GGATGGAAAAGTTGTATCAT 3'           -
I (LH2):  5' AGACCAATTTCTCTTATGAA 3'           +
J (ALU):  5' GGTGAAATCCTGTCTCTACTAAAAA 3'      +++
```

The probability that the DNAs from normal and tumor tissues showing differences in the mobility of some bands did not correspond to the same individuals, reached in some cases values lower that 10$^{-7}$, by the combined analysis of polymorphisms observed with different primers. This figure was reached including polymorphisms for other markers determined by other methods and by criteria other than AP-PCR, including allelic composition determined by standard PCR of (CA)$_n$ repeats and RFLP by Southern blots for polymorphic probes specific for some chromosomes. Two cases in the panel of 139 DNA pairs that we analyzed were discarded because the AP-PCR DNA fingerprints indicated that they did not correspond to the same individuals.

Cloning and Sequence Analysis of AP-PCR DNA Fragments

DNA fragments were excised and eluted from the gels (Almoguera, et al., 1988), reamplified with the same arbitrary primer, cloned in plasmid vectors and sequenced using Sequenase (United States Biochemical, Cleveland, Ohio) as described (Peinado, et al., (1992) *Proc. Natl. Acad. Sci. U.S.A.*, 89: 10065–10069). Once the nucleotide sequence of AP-PCR DNA fragments was determined, cycle sequencing directly from genomic DNA was also possible using specific PCR primers (see Example 4). Briefly, genomic sequences were amplified by PCR (Saiki, et al., 1985; Mullis and Faloona, 1987) with specific primers APΔU and APΔD (see below). One microliter of the PCR product was added to a mix containing PCR buffer, 12.5 μM of J primer in a volume of 35 μl of this solution were added to 7.5 μl of each of the four ddNTPs (Pharmacia), dissolved in PCR buffer. The final concentrations of ddNTPs were 40 μM ddGTP, 250 μM ddATP and ddTTP and 200 μM ddCTP. The reaction was performed for 35 cycles (30 seconds at 95° C., 30 seconds at 55° C. and 1 minute at 72° C.). Samples were diluted with formamide loading buffer, heat denatured and aliquots of 2 μl analyzed in a sequencing gel for 3 hours at 50W. The nucleotide sequence of APΔ3 DNA fragment excised from AP-PCR gels was also determined by cycle sequencing using only one of the arbitrary B or C primers. The nucleotide sequences of the entire APΔ1 (SEQ ID NO: 23 and 24), APΔ2 (SEQ ID NO: 25 and 26) and APΔ3 (SEQ ID NO: 27) DNA fragments are provided in FIGS. 3, 4, and 5, respectively. The de novo mutations (insertions and deletions) observed in simple repeated sequences in USM+ tumors is shown in FIG. 6.

PCR of AP-PCR DNA Fragments

The primers used for standard PCR amplification of the APΔ2 sequences were APΔ2U; 5' TATCTGGGTCT-GAATATGTCTTGGA 3' (SEQ ID NO: 11) and APΔ2D: 5' TGATCATATTGAAATTAAAATCAAA 3' (SEQ ID NO: 12). This PCR generated a 460bp DNA fragment comprising an Alu repeat. The J primer (see above) internal to the Alu repeat, was used for a heminested PCR amplification (see below) of a 278 bp DNA fragment after the initial PCR amplification (15 cycles) of the 460 bp fragment. This heminested PCR amplification was necessary to generate a DNA fragment sufficiently small to yield clear differences in mobility of bands differing in only a few base pairs. The combination of primers APΔ2D and J did not yield consistent amplifications because the last primer was contained inside the repeated Alu sequences.

The primers used for the PCR amplification of the APΔ3 sequences were APΔ3U: 5' GAGGCCCAGCAATCTG-CACT 3' (SEQ ID NO: 13) and APΔ3D: 5' AAATCAG-TATAAGAAAGGAA 3' (SEQ ID NO: 14). This PCR generated a DNA fragment of 150 bp, comprising the run of dA:dTs. Amplification of the 3' end untranslated sequences of the c-K-ras gene (Kahn, et al., 1987) was done using PCR primers K3U: 5' TAAATGAGTTCTGCAAAACAGG 3' (SEQ ID NO: 15) and K3D: 5' ATCTTCATGCAAT-GAAAAATAC 3' (SEQ ID NO: 16). This PCR generates a DNA fragment of 337 bp. In all cases, the relative orientation of the primers (U: upstream; D downstream) is given by the deoxyadenine strand. PCR amplifications were performed for 30 cycles (15 seconds at 94° C.; 15 seconds at 55° C.; 30 seconds at 72° C.) using α-$^{32}$P-dCTP or α-$^{35}$S-dATP, and the radioactive PCR products were analyzed by native polyacrylamide gel electrophoresis as described (Peinado, et al., (1992) *Proc. Natl. Acad. Sci. U.S.A.*, 89: 10065–10069)

The primer J was also used in a high stringency PCR reaction, to amplify Alu repeats located in the genome at relatively short distances and in a head to head orientation (Sinnet, et al., 1990). The reactions were carried out using 50 μg of genomic DNA in PCR buffer containing 2 μM primer J, 0.5 μCi α-$^{35}$S-dATP and one unit of Amplitaq. PCR was performed for 35 cycles of 1 minute at 95° C., 30 seconds at 58° C. and 90 seconds at 72° C. PCR samples were analyzed by denaturing polyacrylamide gel electrophoresis as before.

EXAMPLE 2

Identification of Deletion-Containing Sequences and Normal Flanking Sequences

The deletion-containing sequences identified using the Arbitrarily Primed-PCR methods disclosed above were subjected to PCR using the primers used for arbitrarily primed PCR that additionally have a convenient restriction endonuclease site such as EcoRI extending from the 5' end of the primer. The PCR conditions and reagents are described and provided in the PCR kits available from Stratagene (La Jolla, Calif.). Sequences amplified in the PCR reaction, now containing Eco RI restriction endonuclease sites are extracted with phenol/chloroform and digested with Eco RI and inserted into a vector suitable for DNA sequencing. In this example, the inserts are ligated to pBluescript II SK +/− that was previously digested with Eco RI. Following ligation, the mixture is introduced into competent XL1-blue *E. coli* available from Stratagene, following the transformation protocol included with the bacteria. The transformation mixture is plated onto LB plates containing IPTG and ampicillin. White colonies (those containing inserts) are expanded in ampicillin; the DNA is purified; and the inserts are sequenced using compatible sequencing primers such as the KS primer or the SK primer available from Stratagene and following the priming and extension reactions as disclosed in the Thermalbase® sequencing kit also available from Stratagene. Methods for preparing the dideoxysequencing gels and the apparati required are well known in the art and are available from Stratagene. The sequences of a panel of clones are determined and this information is used to generate a database of sequences identifying a library of dA:dT regions of the genome that contain deletions associated with the cancers described in this invention. This panel of sequences is used to generate the diagnostic assays disclosed in the examples below.

EXAMPLE 3

Identification of Insertions and Deletions in Tumor Tissue

Somatic mutations are also abundant in SRS other than monotonic runs of dA:dT base pairs in the USM+ tumors. These sequences are the di- and trinucleotide repeats or microsatellites. The mutations in these microsatellites are deletions as in the poly A sequences; however, insertions of one or a few nucleotides also occur.

Several colon carcinoma tumor cell lines were identified which exhibited USM in SRS by AP-PCR and PCR experiments with APΔ1, APΔ2 and APΔ3 sequences. A description of the analysis of the mutation rates for SRS in these tumor cell lines is described below.

Single cell clones were isolated from the colon tumor cell lines LS180 and LS174T (ATCC) using cloning cylinders and grown in mass culture. After 25–50 generations, single cell clones were again isolated in 96 well microtiter plates at increasing dilutions, such that about 30–50% of the wells contained cells. Double cell clones were eliminated by visual microscope inspection of the plates. DNA was prepared from these single cell clones when most of the wells contained cells. The plates were washed twice with PBS followed by addition of 50 μl (50 μg/ml) proteinase K in 10

μg/ml Tris-HCl, pH 7.5, 1 mM EDTA. Plates were incubated for 2 hours at 65° C., then for 15 minutes at 95° C. in a humidified atmosphere. One microliter of DNA was used per PCR reaction.

Figure 8:
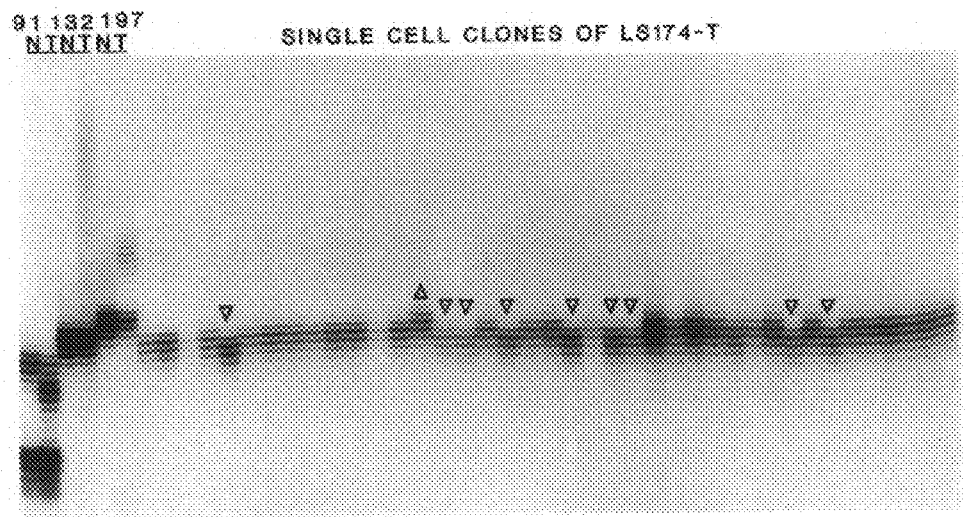
FIG. 8 represents ubiquitous somatic mutations in simple repeated sequences in colon tumor cells in vivo and in vitro. Polymorphic dinucleotide DXS538 sequences were amplified by standard PCR using specific primers obtained from the MAP-PAIRS collection. The numbers on the top left indicate the case number. N=normal tissue; T=tumor tissue. At the right are individual single cell clones isolated in culture from LS-174T colon carcinoma cell line. Triangles point to deletions and inverted triangles point to insertions of DXS538 sequences in individual cell clones.

Polymorphic microsatellite sequences (DXS538) were amplified by PCR with the corresponding PCR primers obtained from Research Genetics, Huntsville, Ala. The resulting PCR products were analyzed on denaturing polyacrylamide gels. The results indicated the presence of insertion as well as deletions. These insertions migrated with a reduced mobility on the gel compared to their normal counterparts (FIG. 8).

EXAMPLE 4

Ligase Chain Reaction (LCR) Diagnostic Kit to Identify Deletion-Associated Neoplasms Example 2 is used to determine the nucleic acid sequences that contain the deletions in the variable regions of DNA associated with Deletion-Associated Neoplasms. Methods identical to those disclosed in Example 2 and in Example 1 are used to determine the sequence of the corresponding sequences from normal tissue that lack deletions. One sequence identified from normal tissue using the methods of Example 1 is provided below (SEQ ID NO: 17):

CGCTATCTACCGCCAT-
AATAAAAAAAAAAAAAAAAATTATCGC-
CGGATAAGACT
GCGATAGATGGCGGTAT-
TATTTTTTTTTTTTTTTTAATAGCG-
GCCTATTCTGA

The corresponding sequence from deletion-associated neoplastic tissue is (SEQ ID NO: 18):

CGCTATCTACCGCCAT-
AATAAAAAAAAAAAAAAAAATTATCGCCG-
GATAAGACT
GCGATAGATGGCGGTAT-
TATTTTTTTTTTTTTTAATAGCGGC-
CTATTCTGA

Therefore, one set of primers useful for detecting the normal sequence in a ligase chain reaction is

```
5' TTTTTTTTTTATTATGGCGGTAGAT 3' (W)(SEQ ID NO: 19)
5' GTTATCCGGCGATAATTTTT 3'      (X)(SEQ ID NO: 20)
5' ACCGCCATAATAAAAAA 3'         (Y)(SEQ ID NO: 21)
5' AAAAAAAAATTATCGCCGGAT 3'     (Z)(SEQ ID NO: 22)
```

Procedures for ligase chain reaction are described in the art. One useful method for performing the ligase chain reaction is provided by Barany et al. (*Proc. Natl. Acad. Sci.* 24 88:189–193, 1991). Patient genomic DNA is isolated from cancerous tissue and normal tissue as described by Higuchi, R. (1989) in PCR Technology: Principles and Applications for DNA amplification, ed. Erlich, H. A. (Stockton, N.Y.), p. 36. Following proteinase K and RNase A digestion, these enzymes are removed by phenol/chloroform extraction. The DNA samples are digested with a restriction endonuclease such as Taq I, or the like. Following a second phenol/chloroform extraction regime to remove the restriction endonuclease, aliquots of the DNA are denatured by boiling for 5 min and rapidly cooled on ice.

The oligonucleotides are endlabelled with $^{32}$P using T4 polynucleotide kinase. Methods and reagents are provided in the KinAce-IT™ kit from Stratagene. Alternatively, chromogenic labels can also be incorporated into the primers and these techniques are well known in the art. Unincorporated $^{32}$P label is removed by chromatography with Sephadex G-25 columns, such as those available from 5'-3', Inc. (San Diego, Calif.). The Ligase Chain Reaction includes 40 fmol of each primer together with 1 fmol Taq I digested DNA in 10 μl of 20 mM Tris.HCl, 100 mM KCl, 10 mM MgCl$_2$, 1 mM EDTA, 10 mM AND$^+$, 10 mM dithiothreitol, 4 μg salmon sperm DNA and 15 nick-closing units of thermostable ligase (Stratagene) and overlaid with a drop of mineral oil. Exemplary reaction conditions are 94 C for 1 min followed by 65 C for 4 min, repeated 15 times. Samples of the reaction (4 μl) are denatured in 45% formamide and denatured by boiling for 3 min and are loaded onto a 10% polyacrylamide gel containing 7M urea in a 100 mM Tris borate buffer. Primer pairs will not be able to amplify sequence corresponding to the normal sequences. The amplified ligase sequence is detected by autoradiography on Kodak XAR-5 film.

This assay generates a positive signal to indicate the presence of deletion-associated neoplasms. It is expected that deletion-associated cancers isolated from a number of individuals will contain a range of deletions in the dA/dT repeat region. To accommodate the diversity of deletion sequences in a region a pool of primers is prepared to account for any number of deletions up to one half of the length of the deletion-associated sequence. Thus, in a string of 18 adenosine residues, primers are designed to account for 3 deletion in the 18 residue sequence up to and including 6 deletions in the 18 residue sequence. Aliquots of primers are used in LCR. The primers W-Z, listed above, are one such example.

It is further contemplated that a kit will be adapted to identify any number of dA:dT regions from the genome identified from methods disclosed in Examples 1 and 2 and that the coordinating primers and primers containing variations in the number of deletions are included to accommodate the identification of those dA/dT sequences.

EXAMPLE 5

PCR diagnostic Kit to Identify Insertion or Deletion-associated Neoplasms

Sequences identified from Example 2 are further sequenced in the upstream and downstream directions to identify conserved regions present on either side of the dA/dT sequences containing deletions. Primer pairs are selected from these conserved regions that bracket the dA/dT regions and are suitable for amplification of the deletion-containing sequences. Methods for selecting suitable PCR primers from a given nucleic acid sequence are known in the art. Details for PCR primer selection are generally available in *PCR Technology: Principles and Applications for DNA amplification*, 1989, ed. Erlich, H. A., Stockton, N.Y.

Matched normal and cancer tissue biopsies are obtained from a patient and genomic DNA is obtained from the tissue using the methods disclosed in Example 1. The DNA is extracted in phenol/chloroform and aliquots are incubated with the four primer pairs either separately or together with appropriate PCR reagents. 0.1 μg of genomic DNA is combined with 50 mM KCl, 10 mM Tris.HCl (pH 8.4), 1.5 mM MgCl$_2$, 100 μg/ml gelatin, 0.25 μM of each primer, 200 μM of each deoxynucleotide triphophate and 2.5 units of Taq polymerase. The cycling profile for the PCR reaction can be optimized as required, however an initial cycling profile is 94° C. for 20 sec., 55° C. for 20 sec., and 72° C. for 30 sec. The cycling is repeated 20 times and finished with a 1.5 min. 72° C. extending step. Example 1 provides an alternative PCR protocol that is also useful for developing a diagnostic method for identifying insertion or deletion-associated neoplasms. Following the PCR reaction, the DNA is loaded onto a polyacrylamide denaturing gel, such as that disclosed in Example 1. The samples are separated and the electrophoretic mobility of the matched fragments from normal and cancerous tissue are compared. Fragments migrating faster than their normal counterparts are determined to contain deletions and fragments migrating slower than their normal counterparts are determined to contain insertions, thereby identifying the cancer as an insertion or deletion-associated type cancer.

EXAMPLE 6

Southern Hybridization Method for the Detection of Insertion or Deletion-Associated Neoplasms As described in the examples above, tissue biopsies from normal and cancerous tissue are removed from a patient. The samples are homogenized and the genomic DNA is isolated. The samples are digested with a restriction endonuclease such as Taq I or Eco RI. Following phenol/chloroform extraction and DNA quantitation (spectrophotometrically at $A_{260/280}$) 5–10 μg of purified DNA is blotted onto prewetted nitrocellulose using a dot-blot manifold (Bio-Rad, Richmond, Calif.). The DNA is linked to the nitrocellulose using a Stratalinker™ (Stratagene). The filters are prehybridized for 24 hours in 3M Tetraethylammonium chloride (TMAC) (Aldrich biochemicals), 0.1 $NapO_4$buffer, pH 6.8, 5×Denhardts solution, 0.6% SDS, 100 μg/ml single strand salmon sperm DNA, 1 M EDTA pH8.0 at 50 C. The filter is hybridized in the same solution containing 250 ng $^{32}$P labelled 30 mer probe that corresponds to the normal sequence associated with a particular insertion or deletion-associated sequence identified from Examples 1 and 2 at 55° C. for 18–24 hours.

Following hybridization, the filters are washed in 3M TMAC with 0.6% SDS in 3×SSC. Since the melting temperature for a 30 mer in 3M TMAC is 74° C., the temperature of the wash solution is initially 55° C. Following a series of 3 washes at 55° C., the filter is exposed to Kodak X-AR X-ray film. The probe will have hybridized to both the DNA from the normal tissue and the DNA from the cancerous tissue. The filter is rewashed at 64° C. and re-exposed to X-ray film. Successive washes are performed in increasing temperatures. As the wash temperature approaches the melting temperature for the probe in TMAC, probe bound to sequence that is not exactly complementary to the primer will be washed off. With successive washes at increasing temperature, insertions or deletions down to one base pair difference can be recognized. This permits the identification of cancerous tissue containing either deletions in the dA/dT regions or insertions in dinucleotide or trinucleotide repeats.

EXAMPLE 7

Detection of Mutations by RNase A Mismatch Cleavage

RNase A mismatch cleavage is a technique based on the ability of pancreatic ribonuclease (RNase A) to recognize and cleave single-base mismatches in RNA heteroduplexes (Winter et al., 1985). This method can be used to determine the presence of mutations as well as their nature and position. Briefly, hybridizations are performed by incubating about $10^5$ cpm of $^{32}$P labeled RNA probe complementary to a mutated DNA region of interest with hybridization solution (80% formamide, 0.4 M NaCl, 1 mM EDTA, 40 mM Pipes, pH 6.7) containing 1–2 mg of the appropriate RNA sample per ml. The solution is heated to 85° C. for 5 min, transferred to a 50° C. water bath and incubated for 12–16 hours.

After hybridization, RNase A is added. At several time points after incubation at 34° C., reactions are stopped by addition of proteinase K and 20% SDS. Carrier tRNA is then added, followed by extraction with phenol/chloroform and ethanol precipitation. The precipitated RNA is then analyzed on an 8% acrylamide/7 M urea gel.

A kit can be easily prepared by providing for instance a riboprobe corresponding to the APΔ3 sequences containing a short poly A tail (14 "A"s, for instance) (Example 1). This riboprobe (a labeled RNA molecule complementary to these APΔ3 sequences) can be hybridized to total genomic DNA from normal and tumor tissues. The hybrids between the riboprobe and the normal tissue DNA will have a mismatch of about 4 nucleotides. This mismatch will be cleaved by the enzyme, generating two smaller fragments. Hybridization, on the other hand, to DNA from a tumor with a deletion of 4 "A"s in APΔ3 sequences will be a perfect homoduplex, which will be resistant to digestion. Alternatively, a riboprobe can be prepared containing wild type length of the repeated sequence (20 "A"s), that when hybridized to normal tissue DNA will be resistant to digestion but cleaved when hybridized to a tumor DNA with deletions in the APΔ3 sequences. The method can be adapted after PCR amplification of the genomic APΔ3 sequences.

TABLE 1

Distribution of deletions in cloned APΔ3 sequences.

| | Length of the runs of dA:dT base pairs | | | | | | | | | | |
|---|---|---|---|---|---|---|---|---|---|---|---|
| | 11 | 12 | 13 | 14 | 15 | 16 | 17 | 18 | 19 | 20 | 21 |
| NORMAL | 0 | 0 | 0 | 1 | 3 | 5 | 5 | 6 | 4 | 2 | 1 |
| TUMOR | 3 | 3 | 8 | 7 | 1 | 0 | 0 | 0 | 0 | 0 | 0 |

The values represent the number of base pairs in the reiterated dA:dT sequences in independently cloned plasmids from total genomic DNA from normal and tumor tissues of case 197 after in vitro amplification by AP-PCR.

Statistical Methods:

In the studies described above, statistical analyses were performed by calculating the Chi square for the comparison of the observed frequencies of mutations with those expected by a random Poisson distribution, as set forth in FIG. 1. The values were: Poisson distribution for total number of deleted nucleotides: m=147/40=3.675; Chi square=63.91; DF=13;P=4.38×$10^7$. Poisson number for total number of bands with deletions: m=111/40=2.775; Chi square=67.93; DF=13; P=4.46×$10^7$. The average number of deleted nucleotides per band was calculated after correction for the variations in mutation frequency due to the length of the runs of dA:dT base pairs in APΔ2, APΔ3, and Alu c-K-ras sequences (FIG. 2). The average number of deleted nucleotides for APΔ3 sequences (cumulative total number of deleted nucleotides in all 16 tumors: 66/16=4.12), was given an arbitrary value of 1. The average values of deleted nucleotides of the other sequences were corrected relative to this arbitrary value.

TABLE 2

Colorectal carcinomas with ubiquitous somatic deletion mutations in monotonic runs of dA:dTbp.

| Case | 43 | 51 | 61 | 66 | 73 | 89 | 91 | 92 | 132 | 149 | 151 | 197 | 201 | 205 | 211 | 238 | | Tumors with and without deletions. + | − | P* |
|---|---|---|---|---|---|---|---|---|---|---|---|---|---|---|---|---|---|---|---|---|
| AGE | 56 | 67 | 55 | 73 | 72 | 39 | 53 | 37 | 71 | 80 | 78 | 57 | 54 | 49 | 63 | 70 | | 60.87 +/− 12.9 | 65.62 +/− 10.2 | 0.049 |
| SEX | M | F | F | M | F | M | F | M | M | F | F | M | F | M | M | M | (M/F) | 9/7 | 79/42 | 0.32 |
| RACE | W | W | B | B | B | W | B | W | W | B | W | B | B | W | W | W | (W/B) | 9/7 | 91/24 | 0.049 |
| DIFFER.[a] | W | M | M | M | P | | P | M | P | P | M | W | M | P | M | P | (P/WM) | 6/9 | 17/90 | 0.036 |
| LOCAT.[b] | C | A | A | T | C | A | T | R | C | C | C | T | C | R | C | A | (L/R) | 2/14 | 71/38 | 0.0008 |
| INVAS.[c] | A | A | B | B | B | A | B | B | B | B | B | D | C | B | B | B | (+/−) | 2/14 | 68/61 | 0.002 |
| RAS[d] | − | − | − | + | − | − | − | + | − | − | − | − | − | − | − | − | (+/−) | 2/14 | 53/68 | 0.013 |
| P53[e] | − | − | − | − | − | − | N | + | − | + | − | − | − | + | − | + | (+/−) | 4/11 | 62/45 | 0.022 |
| REC[f] | − | − | − | + | − | − | + | − | − | − | + | + | − | N | N | N | (+/−) | 3/9* | 51/32 | 0.019 |
| DEAD[g] | − | − | − | + | − | − | + | − | − | + | − | + | − | N | N | N | (+/−) | 2/9* | 25/47 | 0.23NS |

[a] degree of differentiation
W: well
M: moderate
P: poor
In mixed tumors, the presence of less differentiated phenotype was considered to be the dominant character.
b
C: cecum
A: ascending
T: transversal
D: descending
S: sigmoid
R: rectum
L/R: Left (D + S + R)/Right (C + A + T)
[c] Turnbull's modification of Dukes' classification (Sugarbaker, et al., 1985).
−/+: metastases absent (A + B)/metastases present (C + D).
Includes 19 metastatic carcinomas to the liver, all negative for deletions.
d Presence (+) or absence (−) of mutations at codons 12 and 13 of the c-K-ras or N-ras protooncogenes.
[e] Presence (+) or absence (−) of mutations in the p53 tumor suppressor gene. All four tumors positive for p53 mutations retained the normal allele (4/0 vs 27/70: P = 0.007).
f Recurrent tumors. The mean of follow-up (in months) are 16.33/27.0 for recurrent tumors with or without deletions (P = NS) and 46.04/42.2 for not recurrent tumors and with and without deletions (P − NS), respectively.
g Dead with tumor. Mean of survival are 14.5/18.95 for USM+ and USM− tumors. Means of follow-up for patients alive are 43.1/42.34 for tumors with and without deletions.
*Probabilities were calculated by the Fisher exact test in all cases but for the age, which was calculated by comparison of estimated proofs of variance (T: −1.677, D.F. = 130).
N: not analyzed.

REFERENCES

Aaltonen, L., et al. (1993) Clues to the pathogenesis of familial colorectal cancer. Science 260:812–816.

Almoguera, C., et al. (1988) Most human carcinomas of the exocrine pancreas contain mutant c-K-ras genes. Cell 53:549–554.

Ausubel, F. et al., eds., Current Protocols in Molecular Biology. John Wiley & Sons, New York (1989).

Baker, S. J., et al. (1989) Chromosome 17 deletions and p53 gene mutations in colorectal carcinomas. Science 244:217–221.

Barany, F. (1991) Genetic disease detection and DNA amplification using cloned thermostable ligase. Proc. Natl. Acad. Sci. USA 88:189–193.

Beckman, J. S. and Weber, J. L. (1992) Survey of human and rat microsatellites. Genomics 12:627–631.

Bishop, J. M. (1991). Molecular themes in oncogenesis. Cell 64:235–248.

Bos, J. L., et al. (1987) Prevalence of ras gene mutations in human colorectal cancer. Nature 327:293–297.

Bos, J. (1989) in PCR Technology, ed. Erlich, H. A. (Stockton, N.Y.), pp.225–233.

de Jong, D., et al. (1988) Br. J. Cancer 58:773–775.

Fearon, E. R., et al. (1990) Identification of a chromosome 18q gene that is altered in colorectal cancers. Science 247:49–56.

Fearon, E. R. and Vogelstein, B. (1990) A genetic model for colorectal tumorigenesis. Cell 61:759–767.

Fey, M. F., Wells, R. A., Wainscoat, J. S. & Thein, S. L. (1988) J. Clin. Invest. 82:1532–1537.

Foulds, L. The experimental study of tumor progression: A review. (1954) Cancer Research 14:327–337.

Forrester, K., et al. (1987) Detection of high incidence of K-ras oncogenes during human colon tumorigenesis. Nature 327:298–303.

Groden, J., et al. (1991) Identification and characterization of the familial adenomatous polyposis coli gene. Cell 66:589–600.

Harris, C. C. (1991) Chemical and physical carcinogenesis: Advances and perspectives for the 1990s. Cancer Research 51:5023–5044.

Hearne, K. M., et al. (1992) Microsatellites for linkage analysis of genetic traits. Trends in Genetics 8:288–293.

Hudson, T. J., et al. (1992) Isolation and chromosomal assignment of 100 highly informative human simple sequence repeat polymorphisms. Genomics 13, 622–629.

Ionov, Y., et al. (1993) Ubiquitous somatic mutations in simple repeated sequences reveal a new mechanism for colonic carcinogenesis. Nature 363:558–561.

Kahn, S. M., et al. (1987) The c-K-ras gene and human cancer. Anticancer Res. 7:639–652.

Kinzler, K., et al. (1991) Identification of FAP locus genes from chromosome 5q21. Science 253:661–665.

Knudson, A. G. (1971) Mutation and cancer: statistical study of retinoblastoma. Proc. Natl. Acad. Sci. USA 68:820–823.

Knudson, A. G. (1985) Hereditary cancer, oncogenes and antioncogenes. Cancer Res. 45:1437–1443.

Lindahl, T., et al. (1991) Molecular deficiencies in human cancer-prone syndromes associated with hypersensitivity to DNA-damaging agents. Origins of Human Cancer: A Comprehensive Review. Cold Spring Harbor Laboratory Press. Brugge, J., Curran, T., Harlow, E., and McCormick, F., eds. pp. 163–170.

Loeb, L. A., Springgate, C. F., and Battula, N. (1974) Errors in DNA replication as a basis for malignant changes. Cancer Research 34:2311–2321.

Loeb, L. A. (1991) Mutator Phenotype may be required for multistage carcinogenesis. Cancer Res. 51:3075–3079.

Mullis, K. B., and Faloona, F. A. (1987) Specific synthesis of DNA in vitro via a polymerase catalyzed chain reaction. Meth. Enzymol. 155:335–350.

Nacano, H., et al. (1984) Proc. Natl. Acad. Sci. USA 81:71–75.

Nowell, P. (1976) The clonal evolution of tumor cell populations. Science 194:23–28.

Peinado, M. A., Malkhosyan, S., Velazquez, A. and Perucho, M. (1992) Isolation and characterization of allelic losses and gains in colorectal tumors by arbitrarily primed polymerase chain reaction. Proc. Natl. Acad. Sci. USA 89:10065–10069.

Saiki, R., et al. (1985) Enzymatic amplification of B-globin genomic sequences and restriction site analysis for diagnosis of sickle cell anemia. Science 230:1350–1354.

Schimke, R. T., et al. (1986) Overreplication and recombination of DNA in higher eukaryotes: Potential consequences and biological implications. Proc. Natl. Acad. Sci USA 83:2157–2161.

Thein, S. L., et al. (1987) Detection of somatic changes in human cancer DNA by DNA fingerprint analysis. Br. J. Cancer 55:353–356.

Thibodeau, S. N., et al. (1993) Microsatellite instability in cancer of the proximal colon. Science 260:816–819.

Vogelstein, B., et al. (1988) Genetic alterations during colorectal-tumor development. New England Journal of Medicine 319:525–532.

Vogelstein, B., Fearon, E. R., Kern, S. E., Hamilton, S. R., Preisinger, A. C., Nakamura, Y., and White, R. (1989). Allelotype of colorectal carcinomas. Science 244:207–211.

Weber, J. L. and May, P. E. (1989) Abundant class of human DNA polymorphisms which can be typed using the polymerase chain reaction. Am. J. Hum. Genet. 44:388–396.

Weber, J. L. (1990) Informativeness of human $(dC-dA)_n \cdot (dG-dT)_n$ polymorphisms. Genomics 7, 524–530.

Weber, J. L. and Wong, C. (1993) Mutation of human short tandem repeats. Human Mol. Genetics 2, 1123–1128.

Weinberg, R. A. (1991) Science 254:1138–1146.

Weinstein, I. B. (1991) Mitogenesis is only one factor in carcinogenesis. Science 251:387–388.

Welsh, J., and McClelland, M. (1990) Fingerprinting genomes using PCR with arbitrary primers. Nucleic Acids Res 18:7213–7218.

Welsh, J., Petersen, C., and McClelland, M. (1991) Polymorphisms generated by arbitrarily primed PCR in the mouse: Application to strain identification and genetic mapping. Nucleic Acids Res. 19:303–306.

---

What is claimed is:

1. A method of providing a prognosis for at least one of colorectal, stomach, and pancreatic tumor cells comprising:
obtaining sample containing DNA from a potential colorectal, stomach, or pancreatic tumor; and
analyzing DNA of said sample to determine whether mutations in genomic DNA have occurred, wherein the mutations are at least one of deletions and insertions of one or a few nucleotides in reiterated sequences or microsatellite sequences, wherein the reiterated sequences are characterized as having multiple adjacent occurrences of the same nucleotide, dinucleotide pair or nucleotide triplet, and wherein the microsatellite sequences are characterized as having 1–6 base pair tandem repeats, wherein said tumors having said mutations have a prognosis of at least one of the following:
being less invasive than tumors without said mutations;
having a lower rate of recurrence than tumors without said mutations; and
being less likely to have metastasis than tumors without said mutations.

2. The method of claim 1, wherein said analysis comprises:
amplifying DNA of said sample to obtain an amplification product comprising at least one genomic region ordinarily containing said reiterated sequences; and
comparing the amplified DNA product of said sample to an amplification product comprising the at least one genomic region which does not include said mutations.

3. The method of claim 1, wherein said analysis comprises:
amplifying DNA of said sample with a first set of primers complementary to sequences contained in a region thereof ordinarily containing said reiterated sequences to obtain a tumor sample amplification product;
amplifying DNA of a control sample, said control sample containing DNA from normal tissue, with the first set of primers to obtain a control sample amplification product; and
comparing the tumor sample amplification product to the control sample amplification product.

4. The method of claim 3, wherein said control sample and said tumor sample are obtained from a common patient.

5. A method of providing a prognosis for at least one of colorectal, stomach, and pancreatic tumor cells comprising:
obtaining sample containing DNA from a potential colorectal, stomach, or pancreatic tumor; and
analyzing DNA of said sample to determine whether mutations in genomic DNA have occurred, wherein the mutations are deletions of one or a few nucleotides in reiterated sequences, wherein the reiterated sequences are characterized as having multiple adjacent occurrence of the same nucleotide, dinucleotide pair or nucleotide triplet wherein said tumors having said mutations have a prognosis of at least one of the following:
being less invasive than tumors without said mutations;
having a lower rate of recurrence than tumors without said mutations; and
being less likely to have metastasis than tumors without said mutations.

6. The method of claim 5, wherein said tumor cells are colorectal tumor cells, and said potential tumor is a potential colorectal tumor.

7. The method of claim 5, wherein said analysis is by Southern hybridization or RNase A mismatch cleavage.

8. The method of claim 5, wherein said analysis comprises:
amplifying DNA of said sample to obtain at least one genomic region ordinarily containing said reiterated sequences.

9. The method of claim 8, wherein said amplification is PCR amplification.

10. The method of claim 8, wherein said amplification is arbitrarily-primed PCR amplification, and wherein said arbitrarily-primed PCR amplification is characterized as constituting amplification of random DNA segments with single primers of arbitrarily chosen nucleotide sequences, in which the first cycles of amplification are performed at a low annealing temperature that is raised in subsequent cycles to increase stringency.

11. The method of claim 8, wherein said amplification is ligase chain reaction amplification.

12. The method of claim 8, wherein said amplification occurs only if said deletions have occurred.

13. The method of claim 9, wherein DNA of said sample is amplified to obtain at least two different genomic regions ordinarily containing said reiterated sequences.

14. The method of claim 13, wherein said amplification comprises:
contacting the sample DNA with a first set of primers complementary to sequences contained within a first region thereof ordinarily containing said reiterated sequences; and
contacting the sample DNA with a second set of primers complementary to sequences contained within a second region thereof ordinarily containing said reiterated sequences.

15. The method of claim 14, wherein said amplification further comprises:
contacting the sample DNA with a third set of primers complementary to sequences contained within a third region thereof ordinarily containing said reiterated sequences.

16. The method of claim 10, wherein DNA of said sample is amplified to obtain at least two different genomic regions ordinarily containing said reiterated sequences.

17. The method of claim 11, wherein said amplification occurs only if said deletions have occurred.

18. The method of claim 17, wherein said amplification comprises:
contacting the sample DNA with a first set of primers complementary to a predetermined region of DNA that ordinarily contains said reiterated sequences, said amplification occurring only if a first number of said deletions has occurred in said reiterated sequences contained within said region; and
contacting the sample DNA with a second set of primers complementary to a predetermined region of DNA that ordinarily contains said reiterated sequences, said amplification occurring only if a different, second number of said deletions has occurred in said reiterated sequences contained within said region complementary to said second set of primers.

19. The method of claim 18, wherein said amplification further comprises:
contacting the sample DNA with a third set of primers complementary to a predetermined region of DNA that ordinarily contains said reiterated sequences, said amplification occurring only if a third number of said deletions has occurred in said reiterated sequences contained within said region complementary to said third set of primers, wherein said third number is different from said first and second numbers.

20. The method of claim 5, wherein said analysis comprises:
amplifying DNA of said sample to obtain an amplification product comprising at least one genomic region ordinarily containing said reiterated sequences; and
comparing the amplified DNA product of said sample to an amplification product comprising the at least one genomic region which does not include said mutations.

21. The method of claim 5, wherein said analysis comprises:
amplifying DNA of said sample with a first set of primers complementary to sequences contained in a region thereof ordinarily containing said reiterated sequences to obtain a tumor sample amplification product;
amplifying DNA of a control sample, said control sample containing DNA from normal tissue, with the first set of primers to obtain a control sample amplification product; and
comparing the tumor sample amplification product to the control sample amplification product.

22. The method of claim 21, wherein said control sample and said tumor sample are obtained from a common patient.

23. A method of providing a prognosis for at least one of colorectal, stomach, and pancreatic tumor cells comprising:
(a) obtaining sample containing DNA from a potential colorectal, stomach, or pancreatic tumor;
(b) contacting said sample with primers that are complementary to a predetermined region of said DNA that ordinarily contains reiterated sequences or microsatellite sequences as defined in (d) below;
(c) subjecting said sample and said primers to amplification to amplify said DNA; and
(d) analyzing whether amplification occurs to determine whether mutations in genomic DNA have occurred, wherein the mutations are at least one of deletions and insertions of one or a few nucleotides in reiterated sequences or microsatellite sequences, wherein the reiterated sequences are characterized as having multiple adjacent occurrences of the same nucleotide, dinucleotide pair or nucleotide triplet, and wherein the microsatellite sequences are characterized as having 1–6 base pair tandem repeats wherein said tumors having said mutations have a prognosis of at least one of the following:
being less invasive than tumors without said mutations;
having a lower rate of recurrence than tumors without said mutations; and
being less likely to have metastasis than tumors without said mutations.

24. The method of claim 23, further comprising performing a control assay as follows:
obtaining control sample containing DNA from normal tissue; and
subjecting said control sample to (b) through (d).

25. The method of claim 24, wherein said control sample and said tumor sample are obtained from a common patient.

26. A method of providing a prognosis for at least one of colorectal, stomach, and pancreatic tumor cells comprising:
(a) obtaining sample containing DNA from a potential colorectal, stomach, or pancreatic tumor;
(b) contacting said sample with primers that are complementary to a predetermined region of said DNA that ordinarily contains reiterated sequences as defined in (d) below;

(c) subjecting said sample and said primers to amplification to amplify said DNA; and (d) analyzing whether amplification occurs to determine whether mutations in genomic DNA have occurred, wherein the mutations are deletions of one or a few nucleotides in reiterated sequences, wherein the reiterated sequences are characterized as having multiple adjacent occurrences of the same nucleotide, dinucleotide pair or nucleotide triplet wherein said tumors having said mutations have a prognosis of at least one of the following:

being less invasive than tumors without said mutations;

having a lower rate of recurrence than tumors without said mutations; and being less likely to have metastasis than tumors without said mutations.

27. The method of claim 26, further comprising performing a control assay as follows:

obtaining control sample containing DNA from normal tissue; and subjecting said control sample to (b) through (d).

28. The method of claim 27, wherein said control sample and said tumor sample are obtained from a common patient.

29. The method of claim 26, wherein said amplification occurs only if said deletions have occurred.

30. The method of claim 26, wherein said tumor cells are colorectal tumor cells, and said potential tumor is a potential colorectal tumor.

31. The method of claim 26, wherein the analysis is by Southern hybridization assay.

32. A method of predicting the risk of cancer in a patient comprising:

obtaining sample containing DNA from a potential colorectal, stomach, or pancreatic tumor of a patient; and analyzing DNA of said sample to determine whether mutations in genomic DNA have occurred, wherein the mutations are at least one of deletions and insertions of one or a few nucleotides in reiterated sequences or microsatellite sequences, wherein the reiterated sequences are characterized as having multiple adjacent occurrences of the same nucleotide, dinucleotide pair or nucleotide triplet, and wherein the microsatellite sequences are characterized as having 1–6 base pair tandem repeats, wherein patients in which said mutations are detected are at a higher risk to develop cancer than patients in which said mutations are not detected.

33. The method of claim 32, wherein said analysis comprises:

amplifying DNA of said sample to obtain an amplification product comprising at least one genomic region ordinarily containing said reiterated sequences; and comparing the amplified DNA product of said sample to an amplification product comprising the at least one genomic region which does not include said mutations.

34. The method of claim 32, wherein said analysis comprises:

amplifying DNA of said sample with a first set of primers complementary to sequences contained in a region thereof ordinarily containing said reiterated sequences to obtain a tumor sample amplification product;

amplifying DNA of a control sample, said control sample containing DNA from normal tissue, with the first set of primers to obtain a control sample amplification product; and comparing the tumor sample amplification product to the control sample amplification product.

35. The method of claim 34, wherein said control sample and said tumor sample are obtained from a common patient.

36. A method of providing a prognosis for a patient comprising:

obtaining sample containing DNA from a potential colorectal, stomach, or pancreatic tumor of a patient;

analyzing DNA of said sample to determine whether mutations in genomic DNA have occurred, wherein the mutations are at least one of deletions and insertions of one or a few nucleotides in reiterated sequences or microsatellite sequences, wherein the reiterated sequences are characterized as having multiple adjacent occurrences of the same nucleotide, dinucleotide pair or nucleotide triplet, and wherein the microsatellite sequences are characterized as having 1–6 base pair tandem repeats; and correlating the presence of said mutations in the patient with a prognosis of the patient.

37. The method of claim 36, wherein said analysis comprises:

amplifying DNA of said sample to obtain an amplification product comprising at least one genomic region ordinarily containing said reiterated sequences; and comparing the amplified DNA product of said sample to an amplification product comprising the at least one genomic region which does not include said mutations.

38. The method of claim 36, wherein said analysis comprises:

amplifying DNA of said sample with a first set of primers complementary to sequences contained in a region thereof ordinarily containing said reiterated sequences to obtain a tumor sample amplification product;

amplifying DNA of a control sample, said control sample containing DNA from normal tissue, with the first set of primers to obtain a control sample amplification product; and comparing the tumor sample amplification product to the control sample amplification product.

39. The method of claim 38, wherein said control sample and said tumor sample are obtained from a common patient.

* * * * *